(12) United States Patent
Stevens et al.

(10) Patent No.: US 7,049,152 B2
(45) Date of Patent: May 23, 2006

(54) COLOR AND SHAPE CHANGING POLYMERIC RIBBONS AND SHEETS

(75) Inventors: Raymond C. Stevens, La Jolla, CA (US); Quan Cheng, Riverside, CA (US); Jie Song, Fremont, CA (US)

(73) Assignee: The Regents of the University of California, Oakland, CA (US)

( * ) Notice: Subject to any disclaimer, the term of this patent is extended or adjusted under 35 U.S.C. 154(b) by 289 days.

(21) Appl. No.: 10/096,569

(22) Filed: Mar. 12, 2002

(65) Prior Publication Data

US 2002/0137233 A1 Sep. 26, 2002

Related U.S. Application Data

(60) Provisional application No. 60/275,334, filed on Mar. 13, 2001.

(51) Int. Cl.
| | |
|---|---|
| *G01N 33/545* | (2006.01) |
| *G01N 33/547* | (2006.01) |
| *G01N 33/544* | (2006.01) |
| *G01N 33/92* | (2006.01) |
| *G01N 21/63* | (2006.01) |
| *A61K 9/127* | (2006.01) |

(52) U.S. Cl. ............... 436/531; 436/532; 436/164; 436/172; 436/805; 436/811; 436/817; 436/829; 436/535; 436/71; 424/422; 424/450; 530/391.1; 530/402

(58) Field of Classification Search .......... 436/531, 436/532, 164, 172, 805, 811, 817, 829, 535, 436/71; 424/422, 450; 530/391.1, 402
See application file for complete search history.

(56) References Cited

U.S. PATENT DOCUMENTS

| | | | |
|---|---|---|---|
| 4,859,538 A | 8/1989 | Ribi | |
| 5,156,810 A | 10/1992 | Ribi | |
| 5,415,999 A | 5/1995 | Saul et al. | |
| 5,491,097 A | 2/1996 | Ribi et al. | |
| 5,571,568 A | 11/1996 | Ribi et al. | |
| 5,618,735 A | 4/1997 | Saul et al. | |
| 5,622,872 A | 4/1997 | Ribi | |
| 5,852,127 A | 12/1998 | Belfort et al. | |
| 6,001,556 A | 12/1999 | Charych et al. | |
| 6,020,175 A | 2/2000 | Onda et al. | |
| 6,022,748 A | 2/2000 | Charych et al. | |
| 6,080,423 A | 6/2000 | Charych et al. | |
| 6,183,772 B1 | 2/2001 | Charych et al. | |
| 6,306,598 B1 | 10/2001 | Charych et al. | |

OTHER PUBLICATIONS

H. Bader et al, Faraday Discuss. Chem. Soc. (1986), vol. 81, pp. 329-337.*
F. Saremi et al, Supramolecular Science (1997), vol. 4, No. 3-4, pp. 471-477.*
Bader, H., et al., Liposomes from alpha-omega-dipolar amphiphiles with a polymerizable diene moiety in the hydrophobic chain. J. Polym. Sci. Part A-Polym. Chem. 1986, 20, 1623-1628.
Bandyopadhyay, P. et al., Spontaneous Formation of Vesicles by a Cryptand-Based Bol-Amphiphile. Langmuir 1998, 14, 7537-7538.
Berman et al., Total alignment of calcite at acidic polydiacetylene films: Cooperativity at the organic-inorganic interface. Science 1995, 269, 515-518.
Charych, D. et al., Direct colorimetric detection of a receptor-ligand interaction by a polymerized bilayer assembly. Science, 1993, 261, 585-588.
Charych, D. et al., A 'litmus test' for molecular recognition using artificial membranes. Chem. Biol. 1996, 3, 113-120.
Chen, L. et al., Kinetics and Mechanism of the Rod-to-Vesicle Transition of Block Copolymer Aggregates in Dilute Solution. J. Phys. Chem. B 1999, 103, 9488-9497.
Cheng, Q. et al., Charge-Induced Chromatic Transition of Amino Acid-Derivatized Polydiacetylene Liposomes, Langmuir 1998, 14, 1974-1976.
Cheng, Q. et al., Amino Acid Terminated Polydiacetylene Lipid Microstructures: Morphology and Chromatic Transition. Langmuir 2000, 16, 5333-5342.

(Continued)

*Primary Examiner*—Mary E. Ceperley
(74) *Attorney, Agent, or Firm*—Michelle S. Chew; Lawrence Berkeley National Laboratory

(57) ABSTRACT

The present invention herein provides the design, synthesis and characterization of compositions comprising asymmetric bolaamphiphilic lipids that form extended polymeric ribbons and wide sheets. These compositions may be doped, or interspersed, with various compounds to fine-tune the fluidity and rigidity of the bolaamphiphilic lipid composition, and promote other morphologies of the composition, including fluid vesicles and truncated flat sheets. Upon an increase in pH these compositions undergo a calorimetric and morphological transformation.

15 Claims, 9 Drawing Sheets

OTHER PUBLICATIONS

Dobereiner et al., Budding and fission of vesicles. Biophys. J. 1993, 65, 1396-1403.

Eckhardt et al., Separation of chiral phases in monolayer crystals of racemic amphiphiles. Nature 1993, 362, 614-616.

Escalante, J.I. et al., Shear-Induced Transition of Originally Undisturbed Lamellar Phase to Vesicle Phase. Langmuir 2000, 16, 8653-8663.

Escamilla et al., Bolaamphiphiles: From Golf Balls to Fibers. Angew. Chem. Int. Ed. Engl. 1994, 33, No. 19:1937-1940.

Fendler, J. H. Polymerized Surfactant Vesicles: Novel Membrane Mimetic Systems. Science 1984, 223, 888-894.

Jung et al., A new family of very long chain alpha, omega-dicarboxylic acids is a major structural fatty acyl component of the membrane lipids of *Thermoanaerobacter ethanolicus* 39E. J. Lipid Res. 1994, 35(11): 1057-1065.

Langworthy, T. A., Lipids of bacteria living in extreme environments. Curr. Topics in Membr. Transp. 1982, 17, 45-77.

Lee et al., A Dynamically Regulated Transformation of a Bacterial Bilayer Membrane to a Cross-Linked 2-Dimensional Sheet during Adaptation to Unfavorable Environmental Pressures. J. Am. Chem. Soc. 1998, 120, 5855-5863.

Meglio, C.D., et al., Bolaamphiphilic Phosphocholines: Structure and Phase Behavior in Aqueous Media. Langmuir 2000, 16, 128-133.

Oberdisse, J., et al., Experimental study of the micelle-to-vesicle transition. J. Phys. Chem. B 1998, 102, 1102-1108.

Oda, R., et al., Tuning bilayer twist using chiral counterions. Nature 1999, 399, 566-9.

Ringsdorf, H., et al., Molecular Architecture and Function of Polymeric Oriented Systems—models for the study of organization, surface recognition, and dynamics of biomembranes. Angew. Chem. Int. Ed. Engl. 1988, 27, 113-158.

Saremi, F. et al., Self-Assembled Alternating Multilayers Built-up from Diacetylene Bolaamphiphiles and Poly(allylamine hydrochloride): Polymerization Properties, Structure and Morphology. Langmuir 1995, 11, 1068-1071.

Saremi, F. et al., Deeply Colored Self-Assembled Multilayers of Anionic DPP Bolaamphiphiles and Cationic Polyelectrolytes. Advanced Materials 1996, 8(11): 923-925.

Schnur, J. M., Lipid tubules—a paradigm for molecularly engineered structures. Science 1993, 262, 1669-1676.

Schnur, J.M. et al., Diacetylenic Lipid Tubules: Experimental Evidence for a Chiral Molecular Architecture. Science 1994, 264, 945-947.

Schroder et al., Bimodal solubilization of phospholipid-cholesterol vesicles in 3-[(3-cholamidopropyl)dimethylammonio]-1-propanesulfonate (CHAPS) solutions. Formation of filamentous and helical microstructures depends on negatively charged lipids. Eur. Biophys J. 1996, 25, 67-73.

Selinger, J.V., Theory of cylindrical tubules and helical ribbons of chiral lipid membranes. Phys. Rev. E 1996, 53, 3804-3818.

Song, J. et al., Modulating artificial membrane morphology: ph-induced chromatic transition and nanostructural transformation of a bolaamphiphilic conjugated polymer from blue helical ribbons to red nanofibers. Langmuir 2000, 120, 4873-4874.

Song, J. et al., Morphological manipulation of bolaamphiphilic polydiacetylene assemblies by controlled lipid doping. Chem Phys Lipids. Feb. 2002;114(2):203-14.

Song, X.D. et al., Optical signal transduction triggered by protein-ligand binding: Detection of toxins using multivalent binding. J. Am. Chem. Soc. 1998a, 120, 4813-4814.

Song, X. D., et al., Optical biosensor based on fluorescence resonance energy transfer: Ultrasensitive and specific detection of protein toxins. J. Am. Chem. Soc. 1998b, 120, 11514-11515.

Svenson, S. et al., Formation of Polymerizable Phospholipid Nanotubules and Their Transformation into a Network Gel. Langmuir 1999, 15, 4464-4471.

Thomas, B.N., et al.,. Left- and right-handed helical tubule intermediates from a pure chiral phospholipid. Phys. Rev. E 1999, 59, 3040-3047.

Vie, V., et al., Distribution of ganglioside G(M1) between two-component, two-phase phosphatidylcholine monolayers. Langmuir 1998, 14, 4574-4583.

Viswanathan, R., et al., Spontaneous chiral-symmetry breaking by achiral molecules in a Langmuir-Blodgett-film. Nature 1994, 368, 440-443.

Zheng, Y. et al., Cryo-TEM imaging the flow-induced transition from vesicles to threadlike micelles. J. Phys. Chem. B 2000, 104, 5263-5271.

* cited by examiner

COLOR AND SHAPE CHANGING POLYMERIC RIBBONS AND SHEETS

CROSS-REFERENCE TO PRIOR APPLICATION

This application claims priority benefit of U.S. Provisional Application No. 60/275,334, filed on Mar. 13, 2001, pending, which is hereby incorporated by reference in its entirety.

STATEMENT OF GOVERNMENT SUPPORT

This invention was made during work supported by the U.S. Department of Energy under Contract No. DE-AC03-76SF00098. The government has certain rights in this invention.

BACKGROUND OF THE INVENTION

1. Field of the Invention

This invention relates to the field of biomimetic or lipid-based self-assembling molecular materials and to color-changing biosensing microdevices.

2. Description of the Related Art

Since the early 1980s, considerable attention has been directed towards the fabrication of amphiphilic lipid based self-assembling materials as membrane mimetics for a wide range of applications (Fendler, J. H. *Biomimetic Membranes*: Wiley, New York, 1982; Fendler, J. H. *Science* 1984, 223, 888–894; Ringsdorf, H., et al., *Angew. Chem. Int. Ed. Engl.* 1988, 27, 113–158). Today, these materials are playing important roles in the construction of biosensors (Charych, D. et al., *Science*, 1993, 261, 585–588; Charych, D. et al., *Chem. Biol.* 1996, 3, 113–120; Song, X. et al., *J. Am. Chem. Soc.* 1998, 120, 4813–4814 and 11314–11315), controlled release systems or drug/gene delivery vehicles, synthetic supramolecular immunogens and many other nanomachines. Despite the continuing emergence of new applications, however, fundamentals, such as the relationship between the microscopic morphology of the self-assembled systems and the chemical structure and conformation of their constituent lipids, remain to be elucidated. On the practical side, it continues to be challenging to rationally design well-defined functional materials and quickly access highly ordered assemblies under mild conditions.

One application of self-assembling materials is in the field of biosensors. Previous calorimetric sensors were constructed using polydiacetylene lipids incorporating cell surface receptors (e.g. sialo-lipid or $G_{M1}$ ganglioside). These were assembled into films for the detection of influenza virus (Charych et al., *Science* 1993, 261, 585–8) and a number of bacterial toxins (Charych et al., *Chem. Biol.* 1996, 3, 113–20). See U.S. Pat. Nos. 6,001,556; 6,022,748; 6,080,423. These sensors integrated molecular recognition and signal transduction into one supramolecular assembly. The conjugated polymer backbone provided the signal transduction pathway and responded to binding events by a straightforward color change. The detection feature of these colorimetric sensors allows for unaided visual on-site detection of biological hazards and offers great potential for a variety of household medical or diagnostic applications. Thus biosensors can also aid in the detection of the presence or absence of a virus, bacteria, disease indicators, compounds, etc.

More recently, other cellular components have been coupled to polydiacetylene Langmuir films and liposomes, such as nucleic acids (U.S. Pat. No. 6,306,598), proteins (co-pending U.S. patent application Ser. No. 09/023,898) and amino acids (See Song et al., *Langmuir* 2000, 120, 4873–4874) to create biosensors that allow the detection of biological ligands and analytes.

There are, however, limitations to the use of these amphiphilic lipid-based thin film or vesicle sensors. For example, the fabrication of the thin film sensor requires the Langmuir-Blodgett technique, and the detection sensitivities obtained are yet to be further improved. Typically, layered lipid materials must be painstakingly coaxed to assemble, sometimes under conditions much different than those found in nature, and they have limited stability. Thus, a more stable (less fluid) lipid assembly could increase the signal transduction efficiency of biosensors.

There is also a long standing interest of applying self-assembling amphiphilic lipids to coat traditional metallic bone implants to enhance directed biomineral growth and tissue integration at the tissue-implant interface (Berman et al., *Science* 1995, 269, 515–518). However, such biomimetic approach can only be limited to surface modification. A self-assembling bulk polymer that is capable of inducing biomerialization as well as functioning as structural, rather than surface, scaffold of bone implants is not yet available.

A bolaamphiphilic lipid consists of a hydrocarbon chain as the hydrophobic core, and a hydrophilic polar headgroup on each end of the hydrocarbon chain. It is also referred as a bisfunctional lipid in this invention. An amphiphilic lipid, on the other hand, consists of one hydrocarbon chain as the hydrophobic tail and a hydrophilic headgroup on one end of the hydrocarbon chain. It is also referred to a monofunctional lipid.

Some bacterial lipids are transmembranic, coupled tail-to-tail, with functional headgroups on both the inside and outside surfaces of the cell's membrane. Such a two-headed structure resembles an Argentine gaucho's bola, a rope with a weight at each end—thus the adjective, "bolamphiphilic".

Bolaamphiphilic lipids, or bisfunctional lipids, as employed in the present invention, complement very well many of the limitations of monofunctional lipids and provide improved properties. Some of the improved properties noted are that bolaamphiphiles are capable of forming stable structures such as vesicles, and can maintain fluid phases at fairly large surface areas per molecule (Meglio et al., *Langmuir* 2000, 16, 128–133; Escamilla et al., *Angew. Chem. Int. Ed. Engl.* 1994, 33, No. 19:1937–1940; Bader et al., *Faraday Discuss. Chem. Soc.,* 1986, 81, 329–337). Bolaamphiphiles tend to form well-defined microstructures under mild conditions and have high biological relevance as mimics of natural transmembrane lipids' such as those isolated from the thermophilic anaerobic eubacterium, *Thermoanaerobacter ethanolicus* 39E (Jung et al., *J. Lipid Res.* 1994, 35, 1057–1065). In nature, membrane-spanning bipolar lipids provide extraordinary stability to archaebacteria, a class of microorganisms that resist extreme environmental conditions such as low pH, high temperature, and high salt (Langworthy, T. A., *Curr. Topics in Membr. Transp.* 1982, 17, 45–77). Furthermore, the bacterial bilayer in several species of thermophilic bacteria has been found to undergo structural reorganization in response to these extreme conditions (Lee et al., *J. Am. Chem. Soc.* 1998, 120, 5855–5863). Finally, when structurally different functional groups are installed at the two ends of bolaamphiphiles, for the fabrication of materials with asymmetric interfacial properties properties can be achieved. For instance, when one end of a bolaamphiphile is functionalized with a thio group while the other end modified with a sialogroup, they can be immobilized onto gold surface (via Au—S bond) for the electrochemical detection for influenza virus (via the sialo terminus).

Various studies have suggested that the physical nature of the lipid matrix plays a dominant role in the vesicular budding and fission process (Ringsdorf et al., *Angew. Chem. Internat. Ed. Engl.* 1988, 27, 113–158; Dobereiner et al., *Biophys. J.* 1993, 65, 1396–1403). It is known that both general thermodynamic constraints and the geometry of each amphiphilic molecule present in a lipid matrix are crucial factors in determining the final shape and morphology of the aggregates formed (Israelachvili et al., *J Chem. Soc.—Faraday Trans. II* 1976, 72, 1525–1568). Specifically, chirality and the appropriate geometry of constituent lipids are crucial determinants for the chiral packing of self-assembling materials, which has been considered by many as the driving force for tubular and helical microstructure formations (Thomas et al., *Phys. Rev. E* 1999, 59, 3040–3047; Schnur, *Science* 1993, 262, 1669–1676; Eckhardt et al., *Nature* 1993, 362, 614–616; Viswanathan et al., *Nature* 1994, 368, 440–443; Selinger et al., *Phys. Rev. E* 1996, 53, 3804–3818; Oda et al., *Nature* 1999, 399, 566–9). A number of polystyrene block copolymers have been studied by TEM for their rod-to-vesicle and vesicle-to-rod transitions induced by solvents and dilution (Yu et al., *Langmuir* 1999, 15, 7157–7167; Chen et al., *J. Phys. Chem. B* 1999, 103, 9488–9497). Shear flow-induced, surfactant-based vesicle-to-wormlike micelle and micelle-to-vesicle transitions have been studied by using small angle neutron scattering and TEM (Zheng et al., *J. Phys. Chem. B* 2000, 104, 5263–5271; Oberdisse et al., *J. Phys. Chem. B* 1998, 102, 1102–1108; Mendes et al., *J. Phys. Chem. B* 1997, 101, 2256–2258; Escalante et al., *Langmuir* 2000, 16, 8653–8663). Lipid doping effects on microstructure transitions, however, are relatively less explored (Schröder and Schürholz, *Eur. Biophys J.* 1996, 25, 67–73), especially for polymerizable bolaamphiphilic self-assembling systems.

One fundamental consideration in designing biosensors is the requirement of balance between the rigidity and flexibility of the sensor scaffold. Often times this balance is reflected in the microscopic morphology and the extent of polymerization (which is directly influenced by molecular packing) of the sensor material.

The potential of polymerizable self-assembling bolaamphiphilic lipids to form bulk polymeric material with ordered molecular arrangements at the polymer surface makes them ideal structural templates for applications such as, tissue engineering, especially for the engineering of organic-inorganic composites such as bone.

BRIEF SUMMARY OF THE INVENTION

The present invention herein provides the design, synthesis and characterization of bolaamphiphilic lipids that contain a polymerization unit at the hydrophobic core, a chiral anionic acid head group on one hydrophilic end of the molecule and an oxy acid end group on the other hydrophilic end. When well-aligned, the polymerization units can be cross-linked or "polymerized" to provide a conjugated system with enhanced stability and potentially useful optical properties. Cross-linking or "polymerization" can be accomplished by vortexing a mixture of the bolaamphiphilic lipids and exposing the lipids to UV light, whereby the unsaturated bonds internal to the lipid chains covalently link to their neighbors and cause cross linking among adjacent chains. The result is parallel fibers of polymerized chains, being packed into sheets or ribbons as shown in FIG. 1. This composition is blue and can be characterized as in the shape of flat sheets or right-handed helical ribbons. The materials have highly organized hexagonal packing for flat sheets structures and distorted hexagonal or pseudo-rectangular packing for helical structures. Upon treatment with a mild base, or other physical perturbation, such as heating, the composition changes color to red, and the sheets dissociate in the case of base treatment, as shown in FIG. 1, into directed and undirected lipid assemblies that can be characterized as comprising "nanofibers".

This invention also discloses the design and synthesis of a novel chiral bisfunctional transmembrane diacetylene lipid, L-Glu-Bis-3, that rapidly self-assembles into robust right-handed helical ribbon and wide sheet structures under mild conditions. The assemblies are also readily cross-linked to form blue conjugated polymers with retained morphology. The pH sensitivity of the chiral amino acid headgroup of the bolaamphiphile can be used to trigger a morphological transformation of the polymer from blue helical ribbons to red nanofibers, which are further accompanied with a loss of handedness in the packing arrangement. The alignment of the conjugated nanofibers can be controlled through experimental optimization. The color-coded transition between two distinct microstructures opens possibilities in applications where defined molecular templates are the basis for a variety of sensing or triggering mechanisms.

Also herein described by the invention are morphological transformations of asymmetric bolaamphiphilic lipid assemblies from extended wide sheets and helical ribbons to vesicles and truncated flat sheets through controlled doping. The role of lipid dopants in these processes is discussed. Upon doping with a dopant, such as a cell surface receptor, fluid vesicular structures can be induced to emerge, coexisting with the micro-crystalline helical ribbons. The vesicle formation can be further facilitated and stabilized by introduction of a second dopant into the system, presumably through surface curvature variation induced by inhomogeneous distribution and dynamic clustering of the two dopants within the doped assemblies.

In another embodiment, extended wide sheets and helical ribbons are 'truncated' into patches of flat sheets when a sufficient amount of a structurally compatible symmetric bolaamphiphilic lipid is doped into the composition.

Determining the doping-induced morphological transitions from one microstructure to another, and the role that specific lipid dopants play in such transitions provides insight into how changes in chemical composition of the supramolecular assemblies affect the morphological changes observed. By understanding the relationship between assembly composition and morphology, in combination with determining likely morphological transformation mechanisms, efforts in rational design of effective nanomaterials, using these bolaamphiphilic lipids, can be facilitated. These materials can be useful for nano- and micro-applications which include, but are not limited to, synthetic neurons or nerve regeneration, molecular electronics, biosensors and chemical sensors, tissue engineering, and molecular computing devices.

DETAILED DESCRIPTION OF THE PREFERRED EMBODIMENT

Introduction

Figure 1:
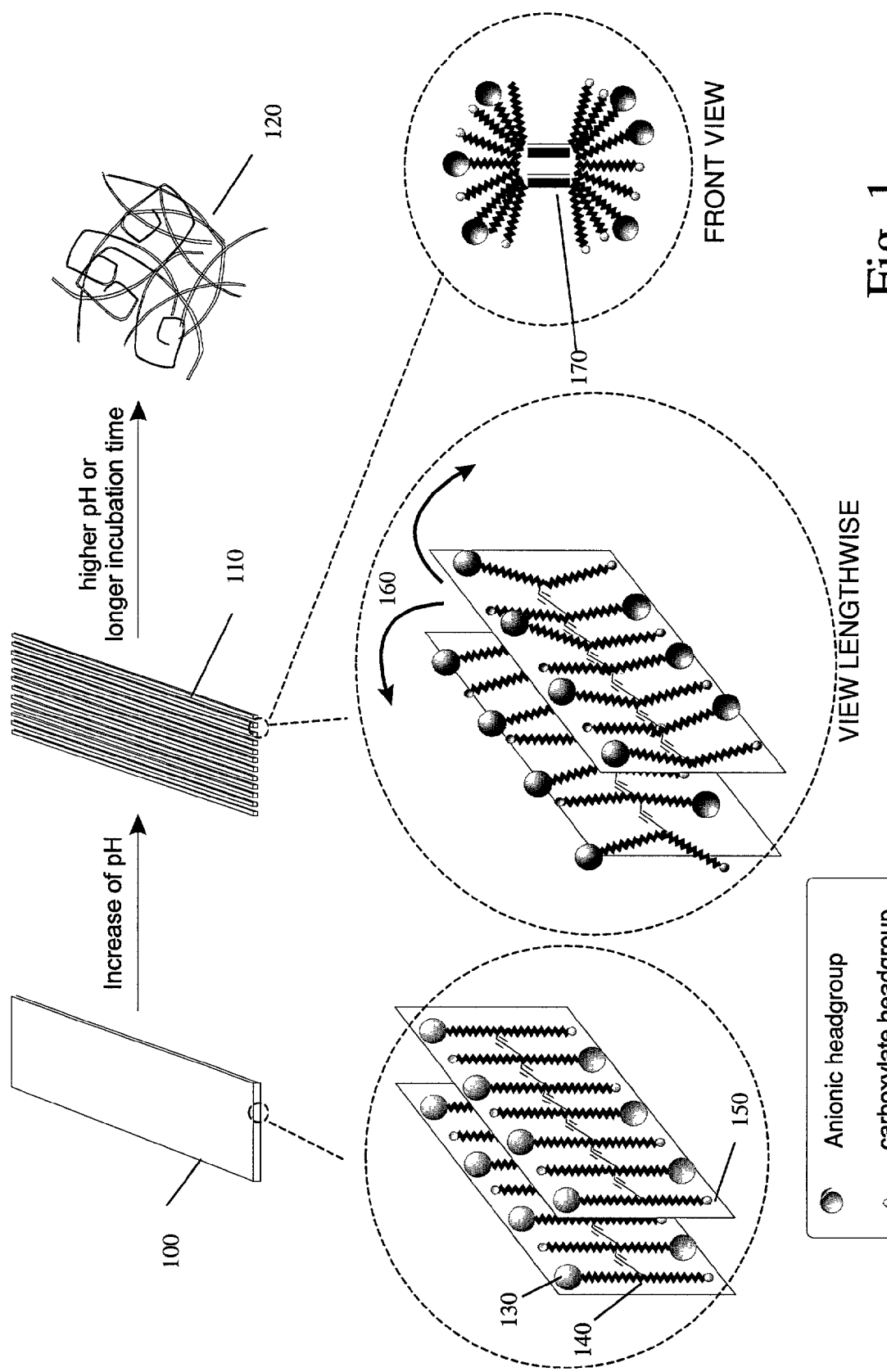
FIG. 1. Representation of the morphological transformation of the present bolaamphiphilic assemblies from wide, flat sheets and helical ribbons (100) to directed nanofibers (110) upon increase in pH. After a longer incubation time or upon increase in higher pH, the nanofibers become randomly coiled (120). The exploded view of the ribbons, shows that the bolaamphiphilic lipids are polymerized into parallel domains, or 'fused fibers'. After the pH increase, electrostatic repulsion (160) between the anionic surface headgroups split the ribbons into nanofibers (110), with the parallel alignment between neighboring ene-yne backbones (170). Also shown in more detail is the anionic headgroups (130), the lipid core (140) and the carboxyl endgroup (150). This morphological change is also accompanied by a color change in composition from blue ribbons to red nanofibers.

The bolaamphiphilic lipids, herein described, are bisfunctional and have a chiral anionic acid head group on one hydrophilic end and an oxy acid end group on the other hydrophilic end of the lipid core. These compositions may be doped, or interspersed, with modified lipids, having instead of an anionic acid head group, a compound designed for molecular recognition.

Bolaamphiphilic lipids have been shown to readily form well-organized systems under mild conditions. Unlike an amphiphilic lipid that forms membrane bilayers, bolaamphiphilic lipids are single units that can organize themselves readily. They mimic transmembrane lipids that some microorganisms synthesize for stabilizing membrane structures in response to extreme conditions such as high pH or temperature (Jung, S. et al., *J. Lipid Res.* 1994, 35, 1057–1065; Lee, J. et al., *J. Am. Chem. Soc.* 1998, 120, 5855–5863). Amino acids have shown to be excellent functional groups for a variety of supramolecular structures, such as vesicles, monolayers, microtubes, ribbons and sheets (Ringdorf, H. et al., *J. Am. Chem. Soc.* 1986, 108, 487–490; Cheng, Q. et al., Langmuir 1998, 14, 1974–1976; Cheng, Q. et al., *Langmuir* 2000, 16, 5333–5342; Cheng, Q. et al., *Thin Solid Films* 1999, 345, 292–299). They render necessary handedness for building chiral supramolecular assembly and provide handles for further surface modifications and improvement of aggregation properties. Preparation and characterizations of this novel material also afford opportunities to examine the underlying structure-morphology-function relationship of bisfunctional chiral self-assembling systems, on both the microscopic and atomic levels.

Definitions

The term "polymerization units" herein refers to the 4-carbon diacetylene group at the center of the bolaamphiphile, upon the polymerization of which, a conjugated ene-yne backbone is formed.

The term "head group" refers to the hydrophilic polar residue (e.g., L-glutamate or carboxylate) attached to the terminus of hydrocarbon core of the bolaamphiphile.

The term "oxy acid" refers to oxygen containing organic acid.

The term "monomers" refers to the molecules that covalently link to each other to form a polymer upon proper initiation, such as by UV irradiation.

The term "self-assembling" refers to the spontaneous organization of amphiphilic or bolaamphiphilic molecules to form an ordered structural aggregate of similar molecules, via energetically favorable van der Walls interaction between the hydrophobic cores and H-bonding on the polar surfaces.

The term "assemblies" refers to the aggregates of a number of molecules; "lipid assemblies" refers to the aggregates of a number of lipid molecules; "bolaamphiphilic assemblies" refers to the aggregates of a number of bolaamphiphilic or bisfunctional molecules.

The term "dopants" herein refers to the molecules added to the aggregates of bolaamphiphilic molecules, either covalently linkable or unlinkable to the bolaamphiphiles, or dispersed in the aggregates of bolaamphiphilic molecules.

Color Changing Polymeric Materials Using Bolaamphiphilic Lipids

A. Materials

1. Synthesis of Bolaamphiphilic Lipids

In general, the bolamaphiphilic lipids of the present invention may be synthesized from commercially available lipid derivatives. These lipids are available with acidic groups at either end. First, the lipid is activated at one end with a good leaving group [e.g. N-hydroxysuccinimide]. Then it is coupled to an anionic headgroup through an amide linkage. The anionic headgroup is preferably an amino acid, and the bolaamphiphilic starting lipid is preferably Bis-1. The synthesis is preferably carried out according to FIG. 2A which shows the preparation of bisfunctionalized diacetylene lipids.

2. The Lipid Core or Polymerization Unit (140)

The lipid core is generally an unsaturated diacetylene lipid, for example, 10,12 docosadiynedioic acid. The lipid could also comprise other diacetylene chains. The conjugation pattern could be, for example, 5,7 or 12,14. The lipid should be at least about a 20 carbon chain to provide an adequate hydrophobic core and up to about 50 carbons in length. The lipid could also comprise other internal cross-linking groups. An advantage of the presently preferred symmetric starting diacetylene lipid, Bis-1, is that it provides an easy synthetic route to the bolaamphiphilic lipids of the present invention.

In other embodiments, the invention contemplates a variety of self-assembling monomers that are suitable for the lipid core. Such monomers include, but are not limited to, acetylenes, diacetylenes (e.g. 5,7-docosadiynedioic acid, 5,7-pentacosadiynedioic acid, 10,12-docosadiynedioic acid and 10,12-pentacosadiynedioic acid), alkenes, thiophenes, polythiophenes, glycopolythiophenes, imides, acrylamides, methacrylates, vinylether, malic anhydride, urethanes, allylamines, siloxanes, anilines, pyrroles, and vinylpyridinium. Lipids containing these groups can be used to form homopolymers or mixed polymers (co-polymers). The composition of the present invention may comprise a single species of self-assembling monomers (e.g. may be made entirely of 5,7-docosadiynedioic acid) or may comprise two or more species. If more than one type of self-assembling monomer is used, solvents containing the individual monomers are combined in the desired molar ratio and then prepared for polymerization.

3. Appropriate Anionic Headgroups (130)

The present bolaamphiphilic lipids contain a polymerization unit in the lipid core (140), an anionic acid headgroup (130) on one hydrophilic end of the molecule and an oxy acid end group (150) on the other hydrophilic end. The headgroup also provides chirality to impart certain physical conformation and preferential chiral packing to the packed sheets or helical ribbons.

Levarotatory (L) amino acids are preferred as the anionic headgroup, however, D-molecules are also contemplated for use with the invention. Glutamic acid is a preferred headgroup, as is aspartic acid. Appropriate molecules for use as an anionic acid headgroup include, but are in no way limited to, anionic chiral amino acids such as glutamate, aspartate, serine, phosphoserine, threonine, glutamine, asparagine and combinations and derivatives thereof. Furthermore, other anionic headgroups are also contemplated including, but not limited to, -DL-Homocystic acid, oxy acids and combinations thereof.

4. Appropriate Oxy Acid End Groups (150)

The oxy acid end group provides a hydrophilic group on the lipid tail for the stabilization of bolaamphiphilic lipid assemblies via enhanced H-bonding formations on both faces of the assemblies. The acid may be a compound such as sulfate, phosphate or other oxy acid. Other oxy acid end groups are also contemplated including, but not limited to, carboxylic acid, hydroxyl groups, amino acids, amino acid derivatives, and other hydrophilic groups. If the desired bolaamphiphile is asymmetric in shape, then it is preferable to use a hydrophilic group that is different from the anionic head group in size. If on the other hand, the desired bolaamphiphile is symmetric, then the it is preferable to choose a hydrophilic group of like size as the anionic headgroup or the same as the anionic headgroup.

B. Preparation and Polymerization

The present invention further comprises methods for making assemblies of bolaamphiphilic lipids capable of changing color. The process comprises providing a mixture of bolaamphiphilic units, along with optional dopants and surface modifying lipids and mixing them, by methods such as vortexing or probe sonication. The lipids will self-assemble into microstructures such as ribbons, sheets, or vesicles. Upon exposure to a cross linking agent such as ultraviolet light, mild vortexing, or sonication, the bolaamphiphilic units become cross linked ("polymerized") through their internal covalent ene-yne bonds (170).

The polymerization of the bolaamphiphilic lipid occurrs rapidly under mild conditions. Instead of probe sonication and subsequent low temperature incubation that are commonly used for mono-functional lipids, vortexing for a short period of time, preferably 2 minutes, and a 10–20 min room temperature incubation is sufficient to ensure the formation of stable supramolecular assembly in aqueous solution. At 0% polymerization, there is no blue color. Between approximately 50 and 80% polymerization is preferred.

UV-irradiation of the assembled material results in rapid polymerization of the bolaamphiphilic lipid within seconds, giving the material a dark blue appearance. The rapid polymerization indicates a highly ordered assembly and the good alignment of diacetylene units. Filtration of the polymerized blue assembly through a 1 µm membrane yields a colorless filtrate that shows no absorption in the visible region indicating the blue polymers are over micron scale in length.

Upon extended incubation, no significant morphological changes are observed, although various degrees of precipitation occur. In a different preparation involving probe sonication and subsequent cooling to room temperature, material with similar morphologies—a mixture of wide sheets and helical ribbons—can be obtained. Thus, mild vortexing and room temperature incubation method is sufficient for the generation of stable materials with defined morphologies.

C. Micro- and Nano-scopic Characterizations—Morphologies and Surface Packing Arrangements Our results in the examples following, demonstrate that bolaamphiphilic lipids are able to form more stable, more compact and better-organized assemblies at ambient conditions, and are therefore suitable for the fabrication of highly ordered functional organic supramolecular assemblies under mild conditions.

Transmission electron micrographs (TEM) confirmed the formation of ribbon-like microstructures with lengths of tens to hundreds of microns in both polymerized and unpolymerized forms. Polymerization of the bolaamphiphilic lipids do not appear to change the morphology of the material. Representative TEM micrographs of the polymeric samples are shown in FIG. 3A. These assemblies contain microstructures in forms of flat ribbons or sheets and twisted ribbons with various degrees of right-handed helicity. Tubular structures may be observed as segments of some helical ribbons, as well as strips of parallel domains on wider ribbons, with apparently the same direction of the polymer backbone. The thickness of the ribbons is between 5 and 10 nm at different regions, suggesting monolayer or double layer packing arrangements, respectively. The widths of the ribbon structures vary from fifty to several hundred nanometers, with generally wider dimension for flat structures.

As illustrated in FIG. 1, the bolaamphiphilic units self assemble and arrange in two possible packing arrangements:

(1) an alternating head-to-tail fashion (shown in FIG. 1), wherein the "head" correlates to the anionic head group and the "tail" correlates to the carboxylate end group, thereby generating two comparable layer surfaces or (2) these bolaamphiphilic units may also be arranged in a head-to-head fashion, wherein the larger anionic acid headgroups pack on the same side of the layer surface generating a biased chiral face with increased curvature. The orientation of the bolaamphiphilic units is determined by thermodynamic and stereoisomeric considerations. The head-to-head orientation tends to cause the cross linked sheets to twist into various helical configurations, rather than the flat sheet.

The alternating arrangement of headgroups may be favorable for the close packing of bolaamphiphilic units because it induces less steric hindrance and electrostatic repulsion between large and more negatively charged glutamic headgroups. This could be the predominant format of organizations when the system first self-assembles into relatively wide flat ribbons. Driven by chiral packing and the further relief of unfavorable headgroup interactions, each assembling lipid would then start to tilt away from its nearest neighbor and lead to the formation of helical structures. Alternatively, the highly biased headgroup arrangement that results in large surface curvatures may also promote the formation of highly twisted helical ribbons.

D. pH-induced Chromatic Transition and Morphological Transformation.

Although new insights continue to be provided for further understanding of chromatic transitions of PDAs, it has been generally accepted that environmental perturbations would induce strains and distortions within the pendant side chains and the conjugated ene-yne backbone (Eckhardt, H. et al., *J. Chem. Phys.* 1986, 85, 4116). Examples of such environmental perturbations have been demonstrated, and are hereby incorporated by reference, as mechanical stress (mechanochromism as disclosed in Galiotis, C. et al., *J. Polym. Sci. Polym. Phys. Ed.* 1983, 21, 2483), high temperature (thermochromism as disclosed in Wenzel, M. et al., *J. Am. Chem. Soc.* 1989, 111, 6123), surface binding events (biochromism as related in Charych et al., *Science,*1993, 261, 585–588; Charych, D. et al., *Chem. Biol.* 1996, 3, 113–120), or extreme pH conditions that cause electrostatic repulsion between the PDA lipids (Cheng, Q. et al., Langmuir 1998, 14, 1974–1976; and Cheng, Q. et al., *Langmuir* 2000, 16, 5333–5342). Such influence results in a shortened conjugation network and absorption of light at a shorter wavelength.

The colorimetric response (CR) of a bisfunctional conjugated polymer can be plotted as a function of pH. A sharp blue-to-red color change is observed upon the increase of pH (graph not shown). Because of the existence of multiple carboxylate groups in the molecule, the chromatic transition occurs at a more acidic pH region compared to the glutamic acid derivatized bilayer polydiacetylene lipids. See Cheng, Q. et al., Langmuir 1998, 14, 1974–1976 and Cheng, Q. et al., *Langmuir* 2000, 16, 5333–5342. At pH 7.5, the bisfunctional conjugated blue polymer studied turned completely red. The UV-Vis absorbance spectra of both red and blue forms of the polymer (also not shown) demonstrate that a chromatic transition occurs when the pH is increased.

The chromatic transition from blue to red can be controlled by pH elevation and exposing the helical ribbons to pH levels of about 5.8 up to 14, preferably at a pH level between about 7.2 and 9.0, and even more preferably at a pH level between about 7.2 to 7.5.

While these chromatic transitions of blue to red have been observed in other PDA assemblies, TEM images of the instant base-treated bisfunctional conjugated polymer show dramatic changes in the morphology of microstructures. All helical ribbons and flat sheets are frayed into thin nanofibers upon the increase of pH (FIGS. 3B, 3C). It appears that the weakly associated network of fibers with defined direction are formed first (FIG. 3B) before they are completely torn apart to form randomly coiled fibers (FIG. 3C). By increasing pH from 7.5 to9 or prolonging the exposure time to these basic conditions, more randomly coiled fibers are observed. The diameters of these fibers are estimated to be below 10 nm. Any pH that is above 5.8 could cause the blue-to-red color change. The pH preference exists in terms of controlling the alignment of nanofibers during the morphological transition from ribbons to fibers. When the pH is too high in that case, randomly coiled instead of oriented fibers will be formed.

From the conditions used to trigger the morphological change, it is apparent that the transformation is caused by increased electrostatic repulsion developed between the deprotonated carboxylate headgroups at higher pH. Higher surface negative charges split closely packed polymer chains and result in thin fibers with less than 10 nm in diameter. FIG. 1 illustrates a model. The front view of the split polymer resembles a tubular micellar block copolymer with stacked conjugated polymer backbones as a rigid core and saturated lipid side chains as floppy arms capped with charged hydrophilic head groups. The pH induced splitting of ribbons to thin nanofibers suggests that linear propagation is the predominant format of polymerization of diacetylene units in this system.

E. Incorporation of Dopants for Dopant-induced Morphological Transformation.

Another aspect of the invention comprises the use of dopants with the disclosed bolaamphiphilic lipids as a direct approach to balance the rigidity and flexibility of the sensor scaffolds for construction of calorimetric sensors. Bolaamphiphilic lipids assemble into a more rigid, semi-crystalline supramolecular structure. However, a certain degree of flexibility of the sensor scaffold must be maintained so that receptor conformation at the membrane surface can be adapted to allow initiation of effective binding events. Such a balance in fluidity may be achieved by lipid doping.

While the incorporation of dopants provides, for example, a binding specificity to a sensor, it also introduces a species that could alter the desirable morphological properties of the biosensor material. From this point of view, lipid-associated receptors could also function as structural dopants of the biosensor scaffold. The shapes of the self-assembled polymerized bolaamphiphilic assemblies may be modified by the incorporations of other compounds or materials, known conventionally as "dopants." Controlled lipid doping, either with a receptor as the only additive or by incorporating additional dopants, provides abundant possibilities to fine-tune the flexibility and morphological properties of the biosensor system.

The bolaamphiphilic lipids form helical ribbons and the like, as previously described, when undoped. Through a selection of dopants, the bolaamphiphilic lipids may be organized into such structures as vesicles, liposomes and flat sheets. Preferred ranges of certain dopants are discussed below. It is recommended that total dopant concentration should not exceed about 20% when a structurally bulky cell surface receptor is used directly as the dopant. The structures of the doped embodiment retain their characteristic blue color and are capable of changing color upon the increase in pH, the binding of an analyte to the molecular recognition of the headgroup or the binding of an analyte to one of the dopants (as demonstrated by the graph in FIG. 6). Based on the transformation of undoped compositions, morphological transformation that accompanies pH elevation of other doped bolaamphiphilic lipid composition structures is also predicted. However, since the doped compositions typically have mixed morphology (e.g. ribbons and vesicles), their morphological change under basic condition is more complicated. However, the ribbons structures from the doped composition are split into nanofibers as well.

1. Types of Dopants.

Dopants allow fine-tuning of the chromatic transition properties of the assemblies and improve the processing properties of the assemblies. Dopants have been contemplated to include, but are not limited to, lipids, cholesterols, steroids, ergosterols, polyethylene glycols, proteins, peptides, or any other molecules such as fatty acids, triacylglycerols, glycerophospholipids, sphingolipids (i.e. sphingomyelins, cerebrosides and gangliosides), sterols, cholesterol, other asymmetric or symmetric bolaamphiphilic lipids (i.e. Bis-1, L-Glu-Bis-3), surfactants, polysorbate, octoxynol, sodium dodecyl sulfate, zwitterionic detergents, decylglucoside, deoxycholate, diacetylene derivatives, phosphatidylserine, phosphotidylinositol, phosphatidylethanolamine, phosphatidylcholine, phosphatidylglycerol, phosphatidic acid, phosphatidylmethanol, cardiolipin, ceramide, lysophosphatidylcholine, D-erythrosphingosine, sphingomyelin, dodecyl phosphocholine, N-biotinyl phosphatidylethanolamine, and other synthetic or natural components of cell membranes that can be associated with a membrane or membrane assemblies such as liposomes and films. In addition, promoter molecules which facilitate chromatic transition in toxin-binding experiments are also contemplated as possible dopants because they possibly function as structural mediators between the non-conjugated receptor molecules and the conjugated backbone of the polymerized bolaamphiphilic lipids. The addition of promoter molecules and other dopants into polydiacetylene compositions has been previously disclosed in by Applicants in U.S. Pat. Nos. 6,183,772 and 6,306,598 which are hereby incorporated by reference in their entirety.

In one embodiment of the invention, the bolaamphiphilic lipid as synthesized by the previous sections can be doped with a ligand or receptor molecule. Ligands can act as the recognition site in the bolaamphiphilic assembly for analytes. Upon the interaction of the analyte with the ligand or ligands, a disruption of the coplaner conjugation of polymer backbone of the bolaamphiphilic matrix lipid occurs, resulting in a detectable color transition. Ligands can be linked through a linking arm (spacer) or directly to a percentage of bolaamphiphilic monomers via various linkages (e.g. —O— or —S— linkages) and incorporated as a dopant prior to or during the polymerization process, or attached to other constituents in the bolaamphiphilic assembly, before, during or following polymerization.

Methods of derivatizing lipids with a diverse range of compounds (e.g., carbohydrates, peptides, proteins, nucleic acids, and other chemical groups) are well known in the art. The carboxylic acid on the terminal end of lipids can be easily modified to form esters, phosphate esters, amino groups, ammoniums, hydrazines, polyethylene oxides, amides, and many other compounds. These chemical groups provide linking groups to attach to carbohydrates, proteins, nucleic acids, and other chemical groups (e.g., carboxylic acids can be directly linked to proteins by making the activated ester, followed by reaction to free amine groups on a protein to form an amide linkage). Examples of antibodies attached to Langmuir films are known in the art (See e.g., Tronin et al., Langmuir 11: 385 [1995]; and Vikholm et al., Langmuir 12: 3276 [1996]). There are numerous other means to couple materials to membranes, or incorporate materials within a membrane, including for example, coupling of proteins or nucleic acids to polymer membranes (See e.g., Bamford et al. Adv. Mat. 6: 550 [1994]); coupling of proteins to self-assembled organic monolayers (See e.g., Willner et al., Adv. Mat. 5: 912 [1993]), and incorporating proteins into membranes (See e.g., Downer et al., Biosensor and Bioelect. 7: 429 [1992]); among others. See Applicant's co-pending U.S. patent application Ser. No. 09/023,898 which discloses a composition and method of coupling proteins to colorimetric biosensors and is hereby incorporated in its entirety. Protocols for attaching ligands (e.g., proteins, nucleic acids, and carbohydrates) to colorimetric materials are known in the art. Such methods are also disclosed by Applicant in U.S. Pat. Nos. 6,306,598 and 6,183,772 and are hereby incorporated in their entirety.

Incorporation of biologically active species, such as proteins, peptides, lipids, or carbohydrates as dopants is also contemplated as an aspect of the invention. In particular, carbohydrates are attractive because they are relatively small when compared to proteins and are expressed externally from the cell surface, for example, as a component of glycoproteins, glycolipids, and capsular polysaccharide. These carbohydrates are involved in key recognition events with a variety of receptor proteins such as hormones, enzymes, toxins, lectins, antibodies, viruses and bacteria. Carbohydrates are also involved in numerous biological processes such as cell growth, recognition and differentiation, cancer metastasis, inflammation and pathogen-entry.

Thus, carbohydrate moieties are excellent tools for creating new types of bolaamphiphilic materials. For example, an analog of sialic acid is the receptor-specific carbohydrate for the Influenza virus, hemagglutinin. In addition, certain mannose residues recognize some bacterial species, such as *E. coli* and *Salmonella*. In particular, Type I piliated *E. coli* is a pathogen responsible for many urinary tract infections, and is a mannose-specific bacteria.

The ligand groups of the present invention can be comprised of a wide variety of materials. The main criterion is that the ligand has an affinity for the analyte of choice. Appropriate ligands include, but are not limited to, peptides, carbohydrates, nucleic acids, biotin, drugs, chromophores, antigens, chelating compounds, molecular recognition complexes, ionic groups, polymerizable groups, dinitrophenols, linker groups, electron donor or acceptor groups, hydrophobic groups, hydrophilic groups, antibodies, or any organic molecules that bind to receptors. The bolaamphiphilic material can be composed of combinations of ligand-linked and unlinked monomers to optimize the desired calorimetric response. Additionally, multiple ligands can be incorporated. As is clear from the broad range of ligands that can be used with the present invention, an extremely diverse group of analytes can be detected.

In some embodiments, ligands are incorporated to detect a variety of pathogenic organisms including, but not limited to, sialic acid to detect HIV, *Chlamydia, Neisseria meningitidis, Streptococcus suis, Salmonella*, mumps, newcastle, and various viruses, including reovirus, Sendai virus, and myxovirus; and 9-OAC sialic acid to detect coronavirus, encephalomyelitis virus, and rotavirus; non-sialic acid glycoproteins to detect cytomegalovirus and measles virus; CD4, vasoactive intestinal peptide, and peptide T to detect HIV; epidermal growth factor to detect vaccinia; acetylcholine receptor to detect rabies; Cd3 complement receptor to detect Epstein-Barr virus; β-adrenergic receptor to detect reovirus; ICAM-1, N-CAM, and myelin-associated glycoprotein MAb to detect rhinovirus; polio virus receptor to detect polio virus; fibroblast growth factor receptor to detect herpes virus; oligomannose to detect *Escherichia coli*; ganglioside $G_{M1}$ to detect *Neisseria meningitidis;* and antibodies to detect a broad variety of pathogens (e.g., *Neisseria gonorrhoeae, V. vulnificus, V. parahaemolyticus, V. cholerae,* and *V. alginolyticus*).

In other embodiments, the invention provides bolaamphiphilic lipids doped with "protein" ligands. Such ligands include, but are not limited to, peptides, proteins, lipoproteins, glycoproteins, enzymes, receptors, channels, and antibodies. Upon binding an analyte (e.g., enzyme substrate, receptor ligand, antigen, and other protein), a disruption of the polymer backbone occurs, resulting in a detectable color change. The present invention contemplates protein ligands that are incorporated onto the bolaamphiphilic lipids and/or other dopants chemically associated with the surface of the bolaamphiphilic matrix lipids (e.g., chemically linked to the surface head group of a monomer in the bolaamphiphilic assembly). For example, when the proteins bind a specific molecule, the proteins undergo a conformational change that induces a color change observed in the bolaamphiphilic assemblies.

2. Effects of Different Dopants.

In general, various types of dopants have different effects upon the morphology and morphological transformation of the present bisfunctional assemblies. Based on the effect of the dopants as illustrated in the Examples of this application and the ease in practicing the invention, one skilled in the art could easily determine the appropriate amount of each dopant to fine tune the flexibility and morphological properties of the biosensor system to be made.

Figure 4:
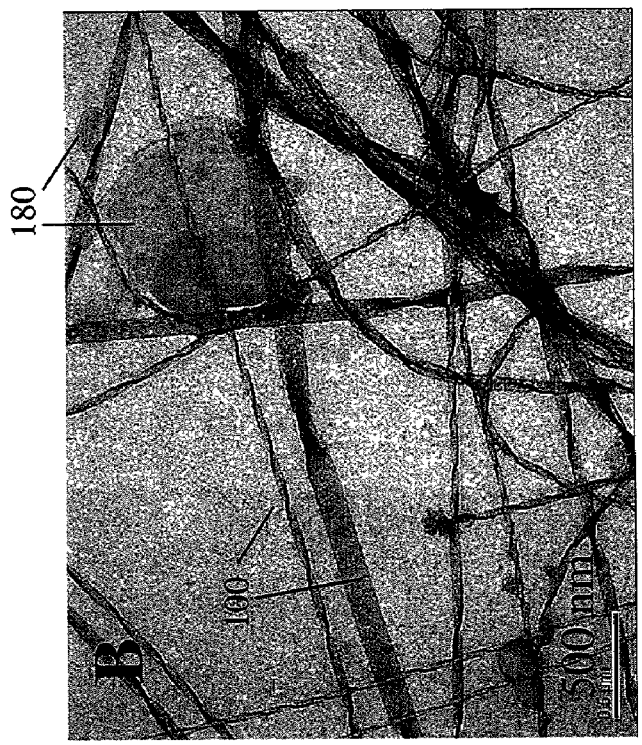
FIG. 4. (A): Transmission electron micrographs of L-Glu-Bis-3 doped with 5% $G_{M1}$ ganglioside. (B): Transmission electron micrographs of L-Glu-Bis-3 doped with 5% $G_{M1}$ ganglioside and 5% cholesterol. Note the appearance of vesicles (180) along with helical ribbons.
Figure 4:
Figure 5:
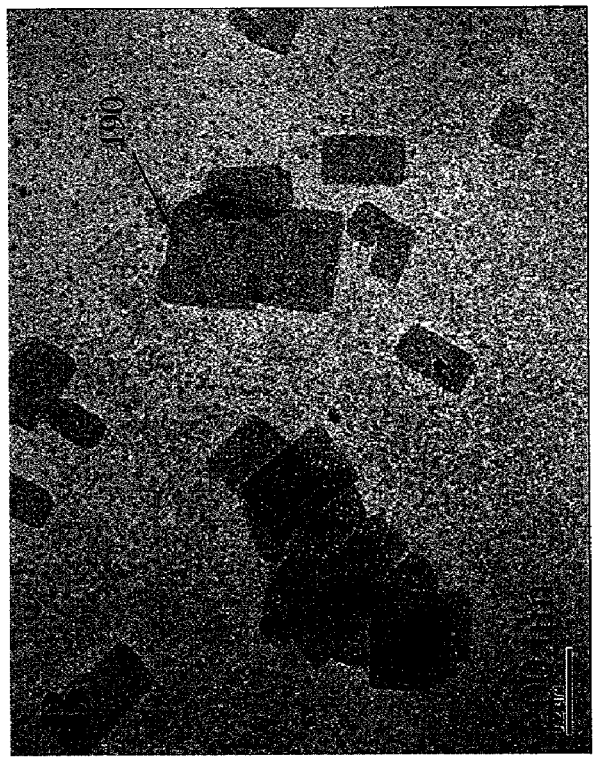
FIG. 5. Transmission electron micrographs of L-Glu-Bis-3 doped with $G_{M1}$ ganglioside and structurally similar bolaamphiphilic lipid Bis-1. (A): L-Glu-Bis-3 doped with 5% Bis-1 and 5% $G_{M1}$ ganglioside. Note the appearance of a small amount of fragmented flat sheets (190). (B): L-Glu-Bis-3 doped with 40% Bis-1 and 5% $G_{M1}$ ganglioside. Note the exclusive formation of patches of flat sheets (190) with (0.1–0.4)μm×(0.1–0.4)μm dimensions.
Figure 5:
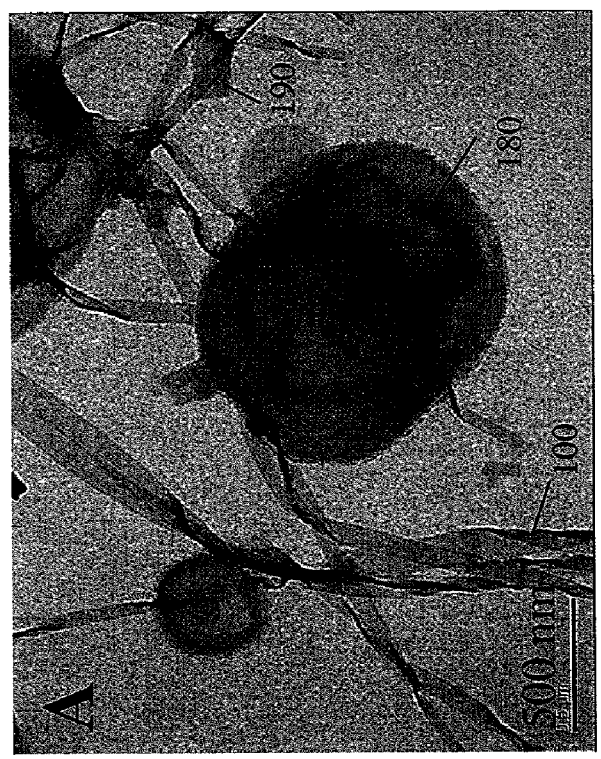

FIGS. 4 and 5 highlight the morphological details of some distinctive microstructures observed for the doped bolaamphiphilic assemblies. It is clear from these micrographs that sheets (very rigid), ribbons (relatively rigid) and vesicles (relatively fluid) are physically interrelated during the formation of different assemblies. Combined with other observations, such as in Example 6, that without inclusion of a dopant such as $G_{M1g}$ ganglioside undoped bolaamphiphilic lipids do not form vesicles but only ribbons and wide sheets, establishes an indisputable role that dopants play a role in promoting vesicle and truncated sheet formation.

What appears to be of particular significance is that controlled doping allows observation of intermediate states in microstructure transition from one form to another. Morphological details of microstructures in doped systems, including domain separation within fluid vesicles, vesicle-to-ribbon transition at the edges of vesicle domains, and the budding and fission of vesicles were all visualized by TEM. The structural influence of the non-polymeric lipid dopants on packing, surface curvature, and fluidity of the assemblies are reflected in domain separation and lateral reorganization.

One skilled in the art need only look to prior studies of various types of molecules associated with cellular membranes to design a dopant strategy. The most appropriate percentage of dopant incorporated with the bolaamphiphilic lipid is dependent on the particular analytic system being developed, and the demands placed on the material. For instance, sensitivity may be compromised to some extent in the favor of longer shelf life, or to accommodate rigorous field conditions. Depending on the type of composition to be made, one could formulate appropriate percentages of each dopant to be mixed with the matrix lipid to fine tune the rigidity and fluidity and the morphological properties of the desired composition.

a. Receptors and Ligands

In one embodiment of the invention, the bolaamphiphilic lipid as synthesized by the previous sections can be doped with a ligand or receptor molecule such as those listed in the previous section. The unique structural and conformational properties of each receptor will contribute to the structural versatility it induces in these microstructures. The incorporation of dopants with bulky headgroups such as oligosaccharides tends to increase the surface curvature of the doped assembly and lead to the formation of vesicular structures. The incorporation of covalently unlinkable, and structurally very different dopants into the system tend to disrupt the crystalline packing of bolaamphiphilic lipids and results in an increased fluidity of the doped supramolecular structure.

b. Gangliosides

In one embodiment of the invention, the bolaamphiphilic lipid as synthesized by the previous sections can be doped with a receptor molecule such as a ganglioside. The unique structural and conformational properties of gangliosides—the bulky pentasaccharide headgroup and ceramide tail—may have contributed to the structural versatility it induces in these microstructures.

Gangliosides are a family of glycosphingolipids localized to the outer leaflet of the plasma membrane of vertebrate cells. They are enriched in neuronal membranes, particularly in synapses (Svennerholm, *Life Sci.* 1994, 55, 2125–34). When inserted into artificial membranes, the oligosaccharide motif of gangliosides is exposed at the membrane surface and functions as recognition groups for a number of bacterial toxins such as Cholera toxin (Song et al, *J. Am. Chem. Soc.* 1998a, 120, 4873–4874; Charych et al., *Chem. Biol.* 1996, 3, 113–20). Gangliosides contain a double-chain ceramide lipid and a rather bulky oligosaccharide headgroup. The size of the ganglioside headgroup is known to dramatically influence the formation of supramolecular assemblies in single lipid formulations. For example, $G_{M3}$ ganglioside, which contains a relatively small trisaccharide headgroup, was shown to undergo spontaneous formation of vesicles with very low bending rigidity in addition to forming lamellar fragments in aqueous solution (Cantu et al., *J. Physique II,* 1994, 4, 1585–1604). For $G_{M1}$ ganglioside, which bears a larger pentasaccharide headgroup, micelle formation was observed at low concentrations (Orthaber and Glatter, *Chem. Phys. Lipids,* 1998, 92, 53–62) and cubic ordering was seen at high concentrations (Boretta et al., *Physica A,* 1997, 236, 162–176).

Thus in a preferred embodiment, the dopant would be a molecule that has analyte-binding capability and possesses a larger headgroup to promote vesicle formation. In a more preferred embodiment, the receptor molecule used to dope the bolaamphiphilic lipid is $G_{M1}$ ganglioside at a molar ratio of not more than 5%. The structure of $G_{M1}$ ganglioside is shown in FIG. 2B. Earlier investigations showed that 5% $G_{M1}$ (molar ratio) added to polydiacetylene films was an appropriate amount to be incorporated into these lipid-based sensors for detection of a variety of toxins (Charych et al., *Chem. Biol.* 1996, 3, 113–20). Therefore, for Example 6, wherein $G_{M1}$ ganglioside was used as a dopant, the $G_{M1}$ content was fixed at this level in the doped systems. When 5% $G_{M1}$ ganglioside was introduced into the L-Glu-Bis-3 system, a fair amount of vesicles were formed along with ribbons, as evidenced by the TEM micrographs in FIG. 3. Inhomogeneous and clustered distribution of $G_{M1}$ ganglioside in the doped assemblies resulted in increase of regional surface curvature, and is believed to be responsible for the generation of vesicular microstructures.

While more than 5% ganglioside can be used to practice the invention, it was observed with an earlier amphiphilic system that incorporation of more than 5% ganglioside degraded the optical properties of the materials containing over 5% lactose derivatized polydiacetylenes. The materials were unstable and sometime underwent calorimetric shifts in the absence of the analyte, perhaps due to ganglioside-induced steric hindrance.

c. Symmetric Achiral Lipids.

In another embodiment of the invention, the bolaamphiphilic lipid is doped with a symmetric achiral lipid to induce a morphological transformation from extended helical ribbons to other shorter sheet structures, such as fragmented flat sheets. In a preferred embodiment, the symmetric achiral lipid is a symmetric achiral lipid structurally similar to the bolaamphiphilic lipid chosen. In a more preferred embodiment, the symmetric achiral lipid is Bis-1 (shown in FIG. 2) if the bolaamphiphilic lipid chosen is L-Glu-Bis-3. Example 6 and FIG. 5 demonstrate the morphological outcome of doping Bis-1 is directly associated with the structural features of Bis-1 as compared to matrix lipid L-Glu-Bis-3.

The transformation from extended helical ribbons wide, flat sheets to shortened flat structures, such as fragmented flat sheets, induced by doping an achiral symmetric lipid into the system suggests a crucial role that the geometry and chirality of constituent lipids plays in the formation of extended helical ribbon structures. Such a dramatic influence of lipid doping on the morphology of the material obtained demonstrates the importance of fine-tuning the specific receptor concentration used in composition formulations.

The truncated sheets are in fact less rigidly packed than extended helical ribbons and the wide, flat sheets formed by undoped bolaamphiphilic lipids. Because of the shortened conjugation in truncated sheets, the blue color appears less intense. Truncated sheets obtained by doping the bolaamphiphilic lipid are also very different from the extended wide sheets that co-exist with ribbons in the pure poly-L-GluBis3 system. The wide sheets observed in the later case are the morphological 'precursor' of the narrow ribbons. Wide flat sheets tend to split along their parallel domain edges to reduce edge energy and then twist to form helical ribbons.

The structural similarity in the lipophilic core segment of the two lipids underlines the high miscibility of the lipids and establishes the role of a symmetric achiral lipid as a structural 'diluting' agent. The difference in size, charge and chirality of the headgroups gives rise to the difference in the geometry of the lipid, the ability of forming H-bonding networks at the surface, the chirality of the assembly at the supramolecular level, and eventually the morphological outcome of the mixed system. Based on our studies, increasing the percentage of a miscible achiral symmetric lipid leads to interruption of the tight, crystalline chiral packing induced by the wedge-shaped bolaamphiphile, ultimately prohibiting the formation of extended helical ribbons, and forming instead patches of flat, rectangular sheets. In a preferred embodiment, the percentage of the symmetric achiral lipid is about 40% or less. Depending upon what the desired morphology of the material to be made will determine the amount of symmetric achiral lipid used to dope the matrix lipid.

d. Structurally Different Lipids

Incorporation of a structurally very different lipid from the bolaamphiphilic lipid chosen, such as cholesterol or other sterol derivatives, was studied up to a 20% molar concentration. Addition of a structurally different lipid, such as cholesterol, that is known to play a role in stabilizing membranes and facilitating vesicle formation, can be used as a dopant to facilitate and stabilize the formation of vesicles. See Ribier et al., U.S. Pat. No. 6,051,250 for a description of other lipid membrane stabilizing agents, such as propylene glycerol alginates and wellan gum, that could be used as dopants in this invention, and Holland et al., U.S. Pat. No. 5,885,613, which discloses a polyethyleneglycol-ceramide conjugate and cholesterol as stabilizing agents of fusogenic liposomes, both which are herein incorporated by reference.

Surfactant type compounds also may serve as dopants. Examples of such surfactant compounds include, but are not limited to, TWEEN 20 and peptide-detergents (i.e. small amphipathic molecules that have a hydrophobic region mimicking the membrane spanning regions of membrane proteins).

The structurally different lipid can be used in combination with other dopants. If used with a dopant known to increase membrane fluidity, addition of the structurally different hydrophobic lipid will prove to increase vesicle formation. For example, the apparent promotion and stabilization of vesicle formation by doping cholesterol, in Example 6, is rationalized as the result of preferential packing of cholesterol in the outer-half of vesicles, where it fills voids between the hydrophobic spaces between $G_{M1}$ ceramide tails and kinked membrane spanning matrix lipid L-Glu-Bis-3. If used with a dopant that increases membrane rigidity, addition of the structurally different lipid will work to offset such rigidity by disrupting the rigid packing of matrix bolaamphiphiles.

At low concentrations of about 5% structurally different lipid, a uniform blue color is still attainable upon UV irradiation. However, as shown in Example 6, with high cholesterol content of about 20%, only turbid suspensions can be obtained. Even after prolonged vortexing or probe sonication, polymerization is difficult. With increased content of structurally different lipids added to the composition, more vesicles are formed with continued coexistence of the ribbon structures (FIG. 4). Therefore, to achieve a significant amount of vesicles attached to ribbons, nested on the framework of entangled ribbons (FIG. 4A) or a material where budding and fission of vesicles are observed (FIG. 4A), the lipid system should be doped with between about 5% and 10% structurally different lipid.

F. Detection of Colorimetric and Morphological Transformation of Bolaamphiphilic Lipids.

Another aspect of the invention comprises the methods of detecting the calorimetric response or pH and dopant-induced morphological transformation properties of the bolaamphiphilic lipids. The colorimetric and morphological transformation of bolaamphiphilic lipids can be detected through various detections methods, including but not limited to, UV-visible spectroscopy, dynamic light scattering experiments (DLS), measuring the spectrophotometric absorbance, transmission electron microscopy (TEM), atomic force microscopy (AFM), Circular Dichroism (CD) Spectroscopy and naked eye detection.

G. Using the Bolaamphiphilic Lipids as Applied to Biosensors

Another aspect of the invention comprises the use of the disclosed bolaamphiphilic lipids for construction of biosensors. Biosensors based upon or incorporating the disclosed bolaamphiphilic lipids can take advantage of the colorimetric and pH and dopant-induced morphological transformation properties of the bolaamphiphilic lipids.

Bolaamphiphilic lipids are more rigid, and therefore are more susceptible to environmental perturbation than polydiacetylene membranes lacking membrane-spanning components. As a result of enhanced rigidity, disturbance on the materials can be more effectively amplified into a detectable change in their absorption properties, resulting in more sensitive colorimetric responses to environmental perturbations. For instance, transmembrane-lipid-containing membranes exhibit sharper pH-induced colorimetric response.

Figure 8:
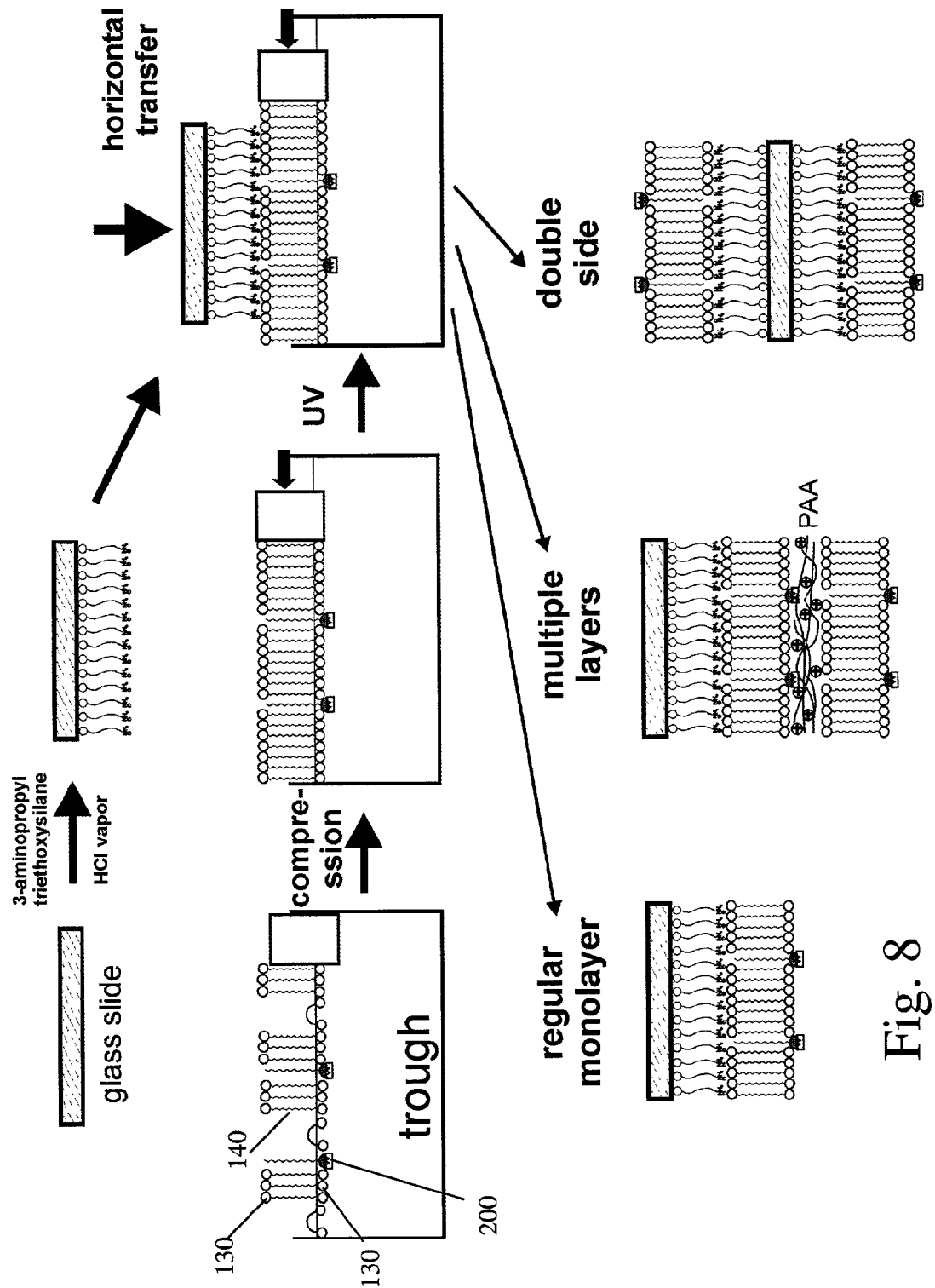
FIG. 8. Representation of a horizontal transfer procedure for making LB films with bolaamphiphilic lipids. Symmetric bolaamphiphilic lipids, having anionic headgroups (130) on both ends of the lipid core (140) and doped with 5% $G_{M1}$ ganglioside (200), can be prepared in a trough for compression and then polymerized. The polymerized transmembranic layer can then be adhered to the protonated surface of chemically modified glass slide via horizontal transfer. Repeating horizontal transfer methods, LB films having a regular monolayer, multiple layers or double-sided films can be made.

Optical and mechanical properties of bolaamphiphilic lipids differ from unifunctional lipids, and a processing method was modified to accommodate the differences. FIG. 8 illustrates the horizontal transfer procedure for making LB films with transmembranic lipids for use as a biosensor. The method of adapted procedure for making LB films with transmembranic lipids for use as a biosensor can be expanded to other types of bisfunctional lipids, either anionically, cationically or neutrally terminated bolaamphiphiles. In the case of using cationically charged bolaamphiphilic lipids to stabilize the LB film sensor, an oppositely charged glass surface treatment will be used. The cationic terminals of the film would then strongly adhere to the negatively charged glass coating.

Doped and undoped bolaamphiphilic lipids can be compressed into monolayers, and horizontal transfer establishes film assemblies that are used as the sensing interface on the treated slides. As illustrated in FIG. 8, double-sided monolayers and multiple layers can be conveniently obtained by adopting various transfer schemes. To bond multiple layers, a polyelectrolyte is preferably used as an adhesion reagent. Examples of an a suitable polyelectrolyte include but is not limited to poly(allylamine) hydrochloride.

H. Using the Bolaamphiphilic Lipids in Future Nano- and Bio-applications

An important aspect of this invention is the ease of controlling microscopic morphology of self-assembling materials using a rationally designed bolaamphiphile. Rational design of bolaamphiphiles is the design of anionic headgroups on both ends of the lipid core as well as the positioning of the polymerization site. Because of the installation of anionic headgroup, this easy-to-assemble material can be morphologically transformed from blue helical ribbons to red nanowires via simple pH elevation. In addition, the morphology of the material can be altered via a straightforward lipid doping approach.

Controlling the morphology of conjugating bolaamphiphilic templates, and in the meantime providing a color-coded measure for the morphological transformation, has significant implication for organic molecule-based nanomaterial and biomaterial research. Potential applications include, but are not limited to, synthetic neurons or neuron repair, molecular electronics (wires and switches), biosensors and chemical sensors, tissue engineering (such as the biomineralization template of bone-like materials), molecular computing devices (note that the morphological change from ribbons to wires is accompanied by the change of surface packing arrangement—see data in Example 4—which indicates that this composition can be a very useful atomic scale template for information process.).

EXAMPLE 1

Synthesis of Bolaamphiphilic Lipids 10,12-Docosadiynedioic acid (Bis-1) was obtained in 95% purity from Lancaster, and was further purified by dissolving it in tetrahydrofuran (THF) and passing it through a short silica pad prior to use to remove blue polymerized impurities. Anhydrous THF used in the lipid activation step was purchased from Aldrich. Water used in the preparation of various buffer solutions was purified with Millipore Milli-Q system. Other chemicals were reagent grade and used without further purification.

For doped bolaamphiphilic lipid assemblies, 10,12-Docosadiynedioic acid (Bis-1) was obtained in 95% purity from Lancaster (Windham, N.H.), and was further purified by dissolving in tetrahydrofuran (THF) with passage through a short silica pad to remove polymerized impurities. Lipid L-Glu-Bis-3 was synthesized by coupling L-glutamic acid with one end of Bis-1 through an amide linkage. Cholesterol (5-cholesten-3-β-ol) was purchased from Sigma (St. Louis, Mo.) in 99+% purity and $G_{M1}$ ganglioside was obtained from Matreya, Inc. (Pleasant Gap, Pa.) in 98+% purity. Both were used without further purification.

EXAMPLE 2

Synthesis of Bolaamphiphilic Lipids

A robust supramolecular assembly requires strong association between assembling units by different forms of intermolecular forces. The classical amphiphilic lipid assembly can be made more rigid via non-covalent approaches such as increasing van der waals interaction via π-π stacking at the lipophilic portion and electrostatic interaction via H-bonding at the hydrophilic portion. The assembly can also be strengthened via covalent modifications such as surface crosslinking, coating, and internal polymerization. See Fendler, J. H. *Science* 1984, 223, 888–894; Ringsdorf, H. et al., *Angew. Chem. Int. Ed. Engl.* 1988, 27, 113–158; Srisiri, W. et al., *J. Am. Chem. Soc.* 1997, 119, 4866–4873.

Here, we designed an L-glutamic acid derivatized wedge-shaped bolaamphiphilic diacetylene lipid L-Glu-Bis-3 (FIG. 2B) as the self-assembling unit of a highly organized molecular architecture. In our design, L-Glutamic acid was attached to one end of a diacetylene-containing lipid 10,12-docosadiynedioic acid (Bis-1) through an amide linkage (FIG. 1). The synthesis of L-Glu-Bis-3 was straightforward. The synthetic route and yields are summarized in FIG. 2A. Commercially available diacetylene lipid Bis-1 was activated on one end with N-hydroxysuccinimide before it was coupled with L-glutamic acid through an amide linkage. The selective activation yielded Mono-NHS-Bis-2 and Di-NHS-Bis-2 in a 4:1 ratio. Mono-NHS-Bis-2 was further converted to L-Glu-Bis-3 with an overall 61% yield. In a modified route, activation of both carboxylate groups before the attachment of glutamic acid and quantitative hydrolysis of the unreacted terminal in the end of the synthesis brought the overall yield up to 87%.

The detailed protocol used is the following. Flash column chromatography was performed on Aldrich silica gel (60 Å, 230–400 mesh). Yields refer to chromatographically and spectroscopically ($^1$H NMR) homogeneous materials. NMR spectra were recorded on a Bruker DRX-500 spectrometer. Chemical shifts are reported relative to the solvent peak. In the case where mixed solvents of methanol, chloroform and water were used, methanol was chosen as the reference. High Resolution Mass Spectrum (HRMS) was recorded on a VG ZAB spectrometer using Fast Atom Bombardment (FAB) condition and an N-benzyl alcohol (NBA) matrix at positive mode.

To a solution of Bis-1 (1.2 g, 3.3 mmol) in THF (50 ml) was added 1-(3-dimethylaminopropyl)-3-ethylcarbodiimide hydrochloride (EDC, 0.7 g, 3.6 mmol) in dichloromethane (20 ml) followed by N-hydroxysuccinimide hydrochloride (NHS, 0.42 g, 3.6 mmol). The mixture was stirred at room temperature overnight followed by the removal of solvent by rotary evaporation. The residue was extracted with chloroform and saturated brine. The organic layer was dried with anhydrous sodium sulfate and concentrated. Pure Mono-NHS-Bis-2 (0.93 g, 61%) was obtained by flash column chromatography. Di-NHS-Bis-2 (0.29 g, 16%) was also isolated along with the recovery of unconverted Bis-1. $^1$H NMR (CDCl$_3$ with trace CD$_3$OD, 500 MHz): δ 2.79 (4H, b), 2.55 (2H, t, J=7 Hz),2.23 (2H, t, J=7 Hz), 2.18 (4H, t, J=7.5 Hz), 1.68 (2H, m), 1.55 (2H, m), 1.45 (4H, m), 1.32 (m), 1.26 (m); $^{13}$C NMR (CDCl$_3$ with trace CD$_3$OD, 125 MHz): δ 176.15, 169.42, 168.41, 76.86, 64.93, 33.60, 30.38, 29.77, 28.65, 28.62, 28.44, 28.29, 28.22, 28.20, 27.87, 27.84, 25.14, 24.43, 24.08, 18.62.

Using the above procedure with excess amount of EDC (2.5 eq.) and NHS (2.5 eq.), Di-NHS-Bis-2 was obtained in multigram scale in >95% yield. $^1$H NMR (CDCl$_3$, 500 MHz): δ 2.84 (8H, b), 2.57 (4H, t, J=7.5 Hz), 2.22 (4H, t, J=7 Hz), 1.71 (4H, t, J=7.5 Hz), 1.49 (8H, t, J=7.5 Hz), 1.37 (m), 1.29 (m); $^{13}$C NMR (CDCl$_3$, 125 MHz): δ 169.18, 168.63, 77.45, 65.25, 30.88, 28.84, 28.73, 28.64, 28.22, 25.56, 24.50, 19.13.

Triethylamine was added dropwise to a suspension of L-glutamic acid (80 mg, 0.54 mmol) in water (5 ml) until a homogenous solution was obtained (pH 8–9). This solution was then slowly introduced to a solution of Mono-NHS-Bis-2 (220 mg, 0.48 mmol) in THF (15 ml). The mixture was stirred for 2 hrs prior to the addition of 3 ml of water and the adjustment of pH to 3 by 1 N hydrochloric acid. THF was removed by rotary evaporation and the remaining aqueous mixture was extracted with ethyl acetate. The organic layer was dried over anhydrous sodium sulfate, filtered and then concentrated by rotary evaporation. The product was purified by flash column chromatography (1:1 chloroform: methanol with 1% v/v water, R$_f$ 0.45) and 204 mg (87%) of L-Glu-Bis-3 was obtained. Similar yield was obtained reacting 0.55 eq. of Di-NHS-Bis-2 with 1 eq. of L-glutamic acid, followed by hydrolysis in aqueous basic solution. $^1$H NMR (CDCl$_3$ and CD$_3$OD with trace D$_2$O, 500 MHz): δ 4.15 (1H, m), 2.20 (m), 1.99 (1H, m), 1.86 (1H, m), 1.55 (4H, m), 1.47 (4H, m), 1.34 (m), 1.27 (m); $^{13}$C NMR (CDCl$_3$ and CD$_3$OD with trace D$_2$O, 125 MHz) δ 176.70, 174.39, 77.15, 77.11, 64.88, 64.85, 48.99, 35.87, 33.83, 28.87, 28.81, 28.71, 28.68, 28.58, 28.49, 28.40, 28.32, 27.92, 27.87, 25.31, 24.53, 18.66; HRMS FAB$^+$ (NBA): C$_{27}$O$_7$NH$_{41}$Na [M+Na]$^+$, calcd 514.2781, found 514.2769.

EXAMPLE 3

Preparation of the Supramolecular Assembly and its Polymerization

Supramolecular Assembly Preparation. The self-assembling of matrix lipid L-Glu-Bis-3 occurred rapidly under mild conditions. Instead of probe sonication and subsequent low temperature incubation that are commonly used for mono-functional lipids, 2 min of vortexing and 10–20 min room temperature incubation was sufficient to ensure the formation of stable supramolecular assembly in aqueous solution for L-Glu-Bis-3. UV-irradiation of the assembled material resulted in rapid polymerization of L-Glu-Bis-3 (within seconds), giving the material a dark blue appearance. The rapid polymerization indicates a highly ordered assembly and the good alignment of diacetylene units. Dynamic light scattering (DSL) indicated that the size of the microstructures was on the scale of microns. Consistent with this, filtration of the polymerized blue assembly through a 1 μm membrane yielded a colorless filtrate that showed no absorption in the visible region.

Undoped Bolaamphiphilic Assemblies. 2 ml of 0.1 N sodium chloride aqueous solution was added to 0.3 mg of L-Glu-Bis-3. The mixture was vortexed for 2 minutes and a clear, colorless solution was obtained. The aggregate was incubated 20 minutes at ambient temperature before UV irradiation or other measurements were taken. For the kinetics study on microstructure formation, the aggregates were incubated for extended time (1 hr, 2 hrs, 5 hrs and 18 hrs) at ambient temperature before UV irradiation was performed. As a control experiment, probe sonication of the lipid suspension was performed for 20 min with a 40 W probe sonicator. The resulting clear solution was allowed to cool to room temperature before another 20 minutes incubation at the same temperature was allowed.

Doped Bolaamphiphilic Assemblies. Three milliliters of 0.1 N sodium chloride aqueous solution was added to 0.9 mg of total lipids, which was a mixture of L-Glu-Bis-3 and 5% G$_{M1}$ ganglioside with 0–20% cholesterol or 0–40% Bis-1 (molar ratios). To obtain stable supramolecular assemblies, three alternative preparation methods were used and compared: vortexing, probe sonication, and heating. In the vortexing procedure, the mixture was vortexed for 2–3 minutes until a clear, colorless solution was obtained. For mixtures with high cholesterol contents (10% and 20%), turbid suspensions were obtained. The assemblies were then incubated at 4° C. for 30 min. For the probe sonication approach, the lipid suspension was sonicated for 20 min with a 40 W probe sonicator. The resulting clear solution was cooled to room temperature before incubation at 4° C. for 30–60 min. The heating method involved heating the mixture at 80° C. for 5 min followed by the same incubation procedure that was used during the probe sonication method. Although all three preparations led to readily polymerizable materials upon UV irradiation, the vortexing method appeared to yield the most homogeneous assemblies, and therefore was chosen as the method of choice for the preparation of all doped assemblies generated in this study.

Crosslinking of the Supramolecular Assemblies. Freshly prepared supramolecular aggregates were loaded onto 96-well polystyrene tissue culture plates and irradiated with UV light (254 nm, CL 1000 Ultraviolet Crosslinker). Crosslinking occurred rapidly and uniform stable dark blue color developed in less than 12 s of exposure time. Longer irradiation (1–2 min) was applied to ensure the formation of extended conjugation networks. The exposure time for various samples ranged from 12 to 60 sec. Longer irradiation time was required for assemblies with high cholesterol content.

EXAMPLE 4

Figure 2A:
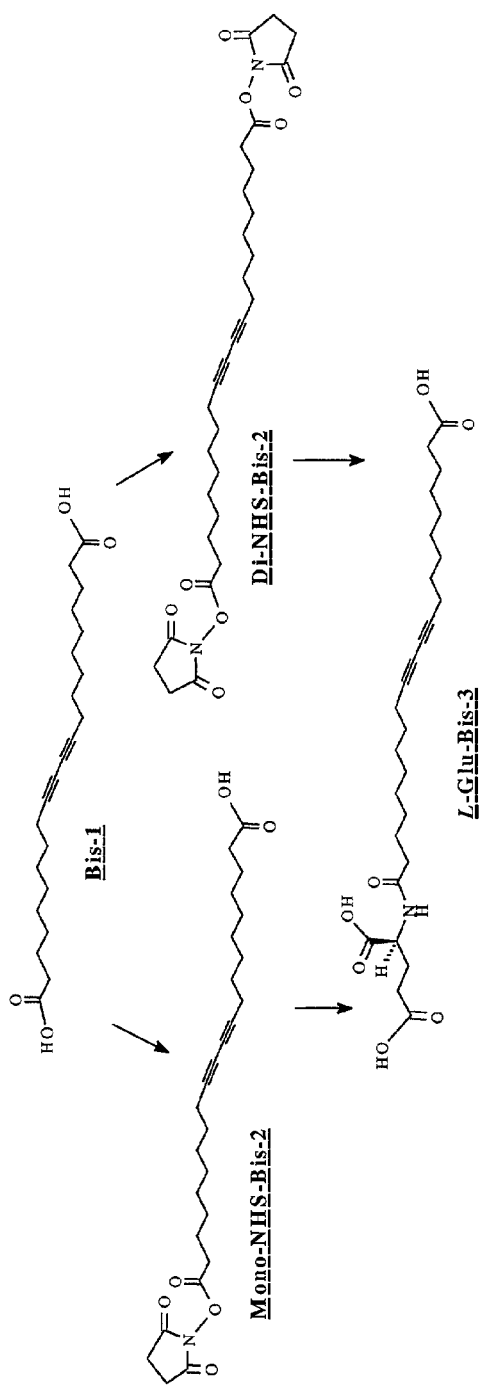
FIG. 2. (A): The synthetic scheme of L-Glu-Bis-3 from Bis-1 by way of the Mono-NHS-Bis-2 and Di-NHS-Bis-2 intermediates. (B): The structures of L-Glu-Bis-3, Bis-1, and dopant molecules, $G_{M1}$ ganglioside and cholesterol.
Figure 2B:
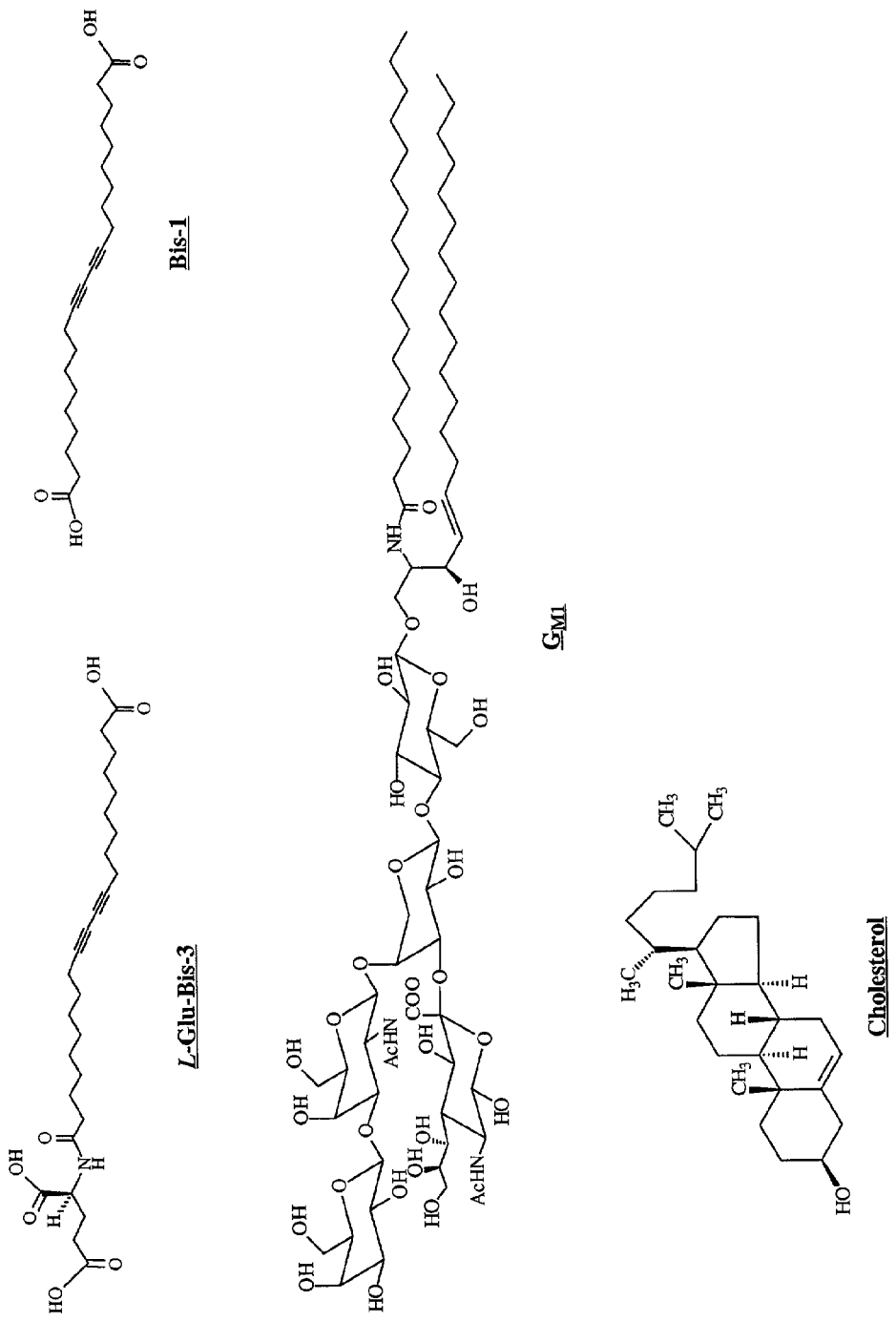

Micro- and Nano-scopic Characteristics—Morphologies and Surface Packing Arrangements Lipid L-Glu-Bis-3 is a wedge-shaped bolaamphiphile conveniently synthesized from symmetric lipid Bis-1 (FIG. 2A). Undoped L-Glu-Bis-3 readily assembles into stable helical ribbons with various degrees of right-handed helicity in an aqueous environment under mild conditions (FIG. 1). In contrast to probe sonication and subsequent low temperature incubation methods that are commonly used for the preparation of mono-functional lipid assemblies, vortexing and room temperature incubation was sufficient to ensure formation of stable supramolecular assemblies of this bisfunctional lipid. Ultraviolet (UV) irradiation of these assemblies resulted in rapid (within seconds) polymerization of L-Glu-Bis-3, affording the material a dark blue color. This rapid polymerization indicated high order structure of the assemblies and good alignment of the diacetylene units. Under TEM, the polymerized material appeared to adopt the same microstructural morphology as unpolymerized L-Glu-Bis-3. These ribbons are up to tens of microns in length. Ribbon thickness is between 5 and 10 nm, suggesting monolayer or double layer packing arrangements at various regions of the microstructures. The widths of the ribbon structures vary from tens to hundreds nanometers for wide, flat sheets, to typically less than a 100 nm width for highly twisted ribbons (FIG. 3A).

Figure 3:
FIG. 3. A series of transmission electron micrographs of poly-L-Glu-Bis-3. (A) shows poly-L-Glu-Bis-3 helical ribbons (100). (B) After treatment with pH 7.5 Tris buffer, poly-L-Glu-Bis-3 ribbons were frayed into nanofibers with defined directions (110). (C) After longer incubation time or higher pH, nanofibers become randomly coiled fibers (120).
Figure 3:
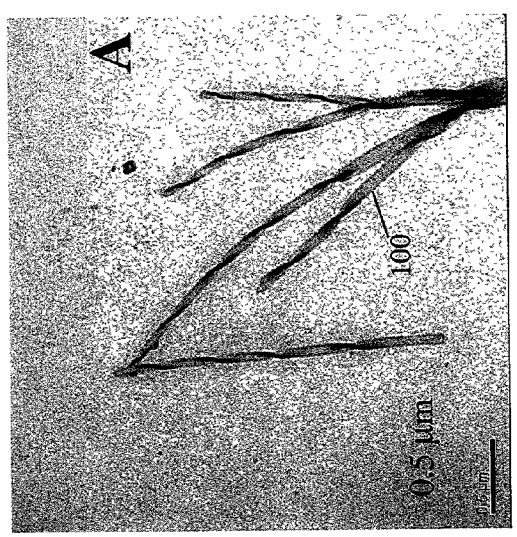
Figure 3:
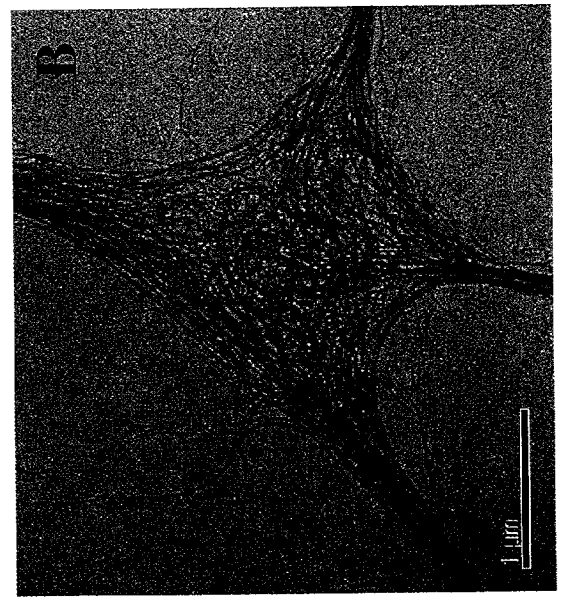

Transmission electron microscopy (TEM) and atomic force microscopy (AFM) were used to characterize the morphology and surface packing arrangement of the material. Transmission electron micrographs confirmed the formation of ribbon-like microstructures with lengths of tens to hundreds of microns in both polymerized and unpolymerized forms. Polymerization of the diacetylenes did not appear to change the morphology of the material. Representative TEM micrographs of the polymeric samples are shown in FIGS. 3. These assemblies contain microstructures in forms of wide, flat sheets and twisted ribbons with various degrees of right-handed helicity. Tubular structures were observed as segments of some helical ribbons, apparently resulting from higher regional helicity. Strips of parallel domains were observed on wider ribbons, with apparently the same direction of the polymer backbone. The thickness of the ribbons was observed between 5 and 10 nm at different regions, suggesting monolayer or double layer packing arrangements, respectively. The widths of the ribbon structures vary from fifty to several hundred nanometers, with generally wider dimension for flat structures.

To address the morphological stability of the observed microstructures, a kinetics study by TEM was conducted. TEM graphs were obtained for samples incubated at room temperature for extended hours (up to 18 hours) before UV crosslinking was conducted. No significant morphological changes were observed (data not shown), although various degrees of precipitation occurred upon extended incubation. This is different from what was observed in a kinetics study conducted on a double chain bilayer PDA lipid, where extended incubation at ambient temperature induced a microstructure transformation from nanotubes to helical ribbons. In a different preparation involving probe sonication and subsequent cooling to room temperature, we obtained the material with similar morphologies—a mixture of wide, flat sheets and helical ribbons.

Extensive experimental discussions and theoretical treatments of the lipid microstructures have been attempted to explain the formation of tubular or helical morphologies. Most theories emphasize the principle of chiral packing. Schnur et al. (*Science* 1994, 264, 945–947; *Science* 1993, 262, 1669–1676) postulated that when bilayer chiral amphiphilic lipids aggregate, they first form large strips with sharply separated domains. When the original aggregate is larger than the favored ribbon width, such aggregates would then break up along the domain edge to form ribbons that are free to twist into helices by chiral packing effect. Helical ribbons may further fuse into tubular structures to reduce edge energy.

Our observations provide evidence to support this theory in the case of a chiral bolaamphiphilic lipid system. TEM micrographs of L-Glu-Bis-3 and Poly-L-Glu-Bis-3 captured the apparent initiation of the transition from flat strips to helical ribbons through rupturing of wider flat strips along the domain or peeling off between two stacked layers. With optimal width and thickness, the smaller strips could then twist into helical structures as a result of these chiral molecules' cumulative tilt away from the local surface normal. Formation of tubular structures, as observed at certain regions, is evidence of further winding of the helical ribbons upon the initial twisting process.

In order to understand the relationship between the microscopic morphology and molecular arrangements, detailed study on the packing of lipids in the assembly at a much smaller scale was performed. We used contact mode AFM to characterize the molecular packing of lipid microstructures on atomic level.

High-resolution scans over a relatively flat helical ribbon surface revealed a highly organized two-dimensional hexagonal packing arrangement at the nanoscopic scale. The bright spots on the AFM image (not shown) represented arrays of terminal carboxylate groups. There are two carboxylates on the glutamate-terminated end of the lipid. One packing scenario is that only the outer terminal carboxylate on the glutamate end is exposed to the surface so that each bright spot on AFM only corresponds to one bolaamphiphilic molecule. In this case, the conventional interpretation of AFM data for alkyl-terminated lipids is applicable. Another possibility is that both carboxylates are exposed to the surface and therefore each glutamate would lead to two bright spots on the surface array. In this case, the assignment of unit cell and the calculation of area per molecule can be complicated.

We believe that the second packing scenario is an unlikely case due to the following reasons: (1) Facing both carboxylates towards the surface would unfavorably expose the hydrophobic alkyl portion of the glutamate towards the aqueous environment; and (2) Isotherms of Langmuir monolayer of analogous glutamate-terminated bilayer diacetylene lipid revealed a limiting molecular area comparable to that for single carboxylate terminated diacetylene lipid, as shown by two of the authors in Cheng, Q. et al., *Langmuir* 1998, 14, 1974–1976, which is hereby incorporated by reference, clearly excludes the packing arrangement where both carboxylates on the glutamate end are exposed to the surface in the crystalline state. Based on one carboxylate per lipid surface exposure, the AFM data analysis can be performed in a conventional way. It is worth pointing out, however, trying to distinguish the terminal carboxylate on the glutamate end from the one on the single carboxylate end, thereby distinguishing biased packing from alternating packing based on this AFM data would be very difficult. The 2-D fast Fourier Transformation (2-D FFT) suggests an approximate cell area of 20 Å$^2$ (a=b=4.8±0.2 Å; γ=60±3°), which is characteristic for tightly packed hydrocarbon chains (Kuzmenko, I. et al., *Langmuir* 1998, 14, 3882–3888).

Unlike previous studies which showed that highly ordered hexagonal packing arrangement could not obtained at room temperature for the blue phase film even when it was over-compressed during the preparation, and instead, pseudo-rectangular packing arrangement was predominantly observed (See Charych et al., *Langmuir* 1997, 13, 6524–6532), our results here demonstrate that L-Glu-Bis-3 is able to form more stable, more compact and better-organized assemblies at ambient conditions, and is therefore suitable for the fabrication of highly ordered functional organic supramolecular assemblies under mild conditions.

Scans of a twisted ribbon area showed a different atomic surface packing arrangement (FIGS. 2C and 2D). 2-D FFT of a typical high-resolution image (FIG. 2C) revealed a pseudo-rectangular unit cell with a cell area of approximately 24 $Å^2$ (a=6.2±0.3 Å; b=3.9±0.3 Å; $\gamma$=90±3°). Two possible scenarios or the combination of increase in unit cell area. First, the increase in unit cell area may be a result of the increased molecular tilt away from the local surface normal at the helical region. Second, relatively loose packing is expected in highly curved region. The system has to be less rigid in areas of curvature and a less closely packed cell such as a highly distorted hexagonal or pseudo-rectangular cell would be more favorable than a hexagonal one.

It is worth noting that when the scanning tip swept through the top of the three dimensional ribbon structure, regional fluctuations would occur and sometimes led to lateral dislocations in the frictional force images. However, similar images were observed over several consecutive scans. The rectangular packing arrangement was still observed in the 2D-FFT. Repeated scans did not cause any damage to either form of the microstructures, suggesting the system's robust organization.

The AFM study of the bisfunctional PDA lipid microstructures demonstrates the difference in packing arrangement between helical ribbon structures and thin films formed by the monofunctional PDA lipid. Moreover, our results reveal that there is a shift in molecular packing and an increase in unit cell dimension when the microstructure undergoes a morphological twist. The results suggest a strong correlation between packing arrangements at the atomic scale and morphologies of the material at micron scale, as characterized by hexagonal and pseudo-rectangular packing arrangements at flat and highly twisted regions of the microstructure, respectively.

EXAMPLE 5 pH-induced Chromatic Transition and Morphological Transformation

Colorimetric properties of the bisfunctional conjugated polymer were studied. As expected, electrostatic repulsion between headgroups caused by pH elevation led to the typical blue-to-red transition of the conjugated polydiacetylene polymer. Data showing the colorimetric response (CR) of Poly-L-Glu-Bis-3 as a function of pH is not shown but herein described. A sharp blue-to-red color change was observed upon the increase of pH. Because of the existence of multiple carboxylate groups in the molecule, the chromatic transition occurred at a more acidic pH region compared to the glutamic acid derivatized bilayer polydiacetylene lipids. At pH 7.5, the Poly-L-Glu-Bis-3 blue polymer turned completely red. The UV-Vis absorbance spectra of both red and blue forms of the polymer were observed in absorbance curves of the red and blue forms of poly-L-Glu-Bis-3. Samples were run in Tris buffer at pH 7.5 in the case of the red form. The absorbance peak at about 0.35 absorbance units, which was observed at about 550 nm for the red form, was shifted from about 625 nm for the blue form.

TEM images of base-treated Poly-L-Glu-Bis-3 showed dramatic changes in the morphology of microstructures. All helical ribbons and flat sheets were frayed into thin nanofibers upon the increase of pH. It appears that the weakly associated network of fibers with defined direction were formed first (FIG. 3B) before they were completely torn apart to form randomly coiled fibers (FIG. 3C). By increasing pH from 7.5 to 9 or prolonging the exposure time to these basic conditions, we were able to observe more randomly coiled fibers. The diameters of these fibers were estimated below 10 nm.

From the conditions used to trigger the morphological change, it is apparent that the transformation was caused by increased electrostatic repulsion developed between the deprotonated carboxylate headgroups at higher pH. Higher surface negative charges split closely packed polymer chains and resulted in thin fibers with less than 10 nm in diameter. An explanation of the model is given in the description of the preferred embodiment. The pH induced splitting of ribbons to thin nanofibers suggests that linear propagation is the predominant format of polymerization of diacetylene units in this system.

AFM characterization of the molecular packing of the nanofibers was attempted. Unfortunately, high fidelity images could not be obtained. These fibers were easily brushed away by the scanning tip due to lack of strong adhesion of the material to the substrate.

An earlier study on mono-functional PDA lipid morphology using AFM showed 10–20 nm wide parallel stripelike features within a single PDA domain (Charych, D. H. et al., *Langmuir* 1997, 13, 6524–6532). Our observation on the formation of 10 nm wide fibers from the splitting along domain edges of wider bisfunctional PDA ribbons in response to pH elevation is consistent with the data from this earlier study. This suggested that the smallest width of optimal subdomains of such PDA aggregations, especially in aqueous solution, could be around or below 10 nm.

In addition to UV-Vis and TEM, we employed other spectroscopic methods, particularly Circular Dichroism (CD) spectroscopy; to characterize the pH induced chromatic transition and morphological transformations. CD spectra can provide empirical evidence of protein and nucleic acid secondary structures. They are also useful in studying chiralities of synthetic self-assembling aggregates where chirality originates from the chiral packing of assembling molecules. A dramatic change in molar ellipticity $\theta$ was observed when the Poly-L-Glu-Bis-3 assembly was transformed from right-handed helical ribbons to frayed fibers by pH increase (FIG. 3). The intense absorption band of Poly-L-Glu-Bis-3 around 200 nm agreed with literature data where the self-assembling of bilayer amphiphilic PDA lipids yielded helical ribbon and tubular structures (Spector, M. S. et al., *Proc. Natl. Acad. Sci. U.S.A.* 1996, 93, 12943–12946 and *Langmuir* 1998, 14, 3493–3500). A comparison between CD spectra of Poly-L-Glu-Bis-3 (data not shown) before and after the base treatment showed an intense absorption band at around 200 nm in the case of Poly-L-Glu-Bis-3 before base treatment. This dramatic loss in molar ellipticity (almost 90%) accompanying the morphological transformation of the assembly, clearly indicates the massive loss of chiral microstructures (helical ribbons and tubes) during the transformation. The new microstructures (nanofibers) formed under basic conditions only passed on an insufficient amount, if any, of the chiral packing arrangement to contribute to the overall chirality in the assembly.

EXAMPLE 6

Morphology of Doped Bolaamphiphilic Lipids

To probe the effect of lipid doping on the microstructural morphology of bisfunctional assemblies, three types of molecules, $G_{M1}$ ganglioside, cholesterol and Bis-1, were chosen as lipid dopants. The structures of these dopants are shown in FIG. 2B. Gangliosides are a family of glycosphingolipids localized to the outer leaflet of the plasma membrane of vertebrate cells. They are enriched in neuronal membranes, particularly in synapses (Svennerholm, *Life Sci.* 1994, 55, 2125–34). When inserted into artificial membranes, the oligosaccharide motif of gangliosides is exposed at the membrane surface and functions as recognition groups for a number of bacterial toxins (Song et al, *J. Am. Chem. Soc.* 1998a, 120, 4873–4874; Charych et al., *Chem. Biol.* 1996, 3, 113–20). Ganglioside $G_{M1}$, a known receptor of cholera toxin (Holmgren et al., *Proc. Natl. Acad. Sci. USA* 1975, 72, 2520–4), was chosen in this work to be incorporated into the assembly of L-Glu-Bis-3. Structurally alien polycyclic lipid cholesterol was selected as a dopant because it is an essential component of biological membranes and also a natural target of streptolysin O, a transmembrane pore-forming toxin (Alouf and Geoffroy, Sourcebook of bacterial protein toxins, Academic Press, London, pp147–186 (1991); Bhakhi et al., *Infect. Immun.* 1985, 47, 52–60) that is another potential detection target of interest. Low concentrations of $G_{M1}$ or cholesterol were shown to modulate domain structure and phase separation in model membrane systems (Hwang et al., *Science* 1995, 270, 610–4). Bis-1 is a symmetric achiral lipid structurally similar to L-Glu-Bis-3, and was used to probe the effect of the geometry and chirality of constituent lipids on microstructure formation.

Incorporation of $G_{M1}$ ganglioside as dopant. The effect of incorporating $G_{M1}$ ganglioside on the morphology of L-Glu-Bis-3 assemblies was investigated. Earlier investigation showed 5% $G_{M1}$ (molar ratio) added to polydiacetylene films was an appropriate amount to be incorporated into these lipid-based sensors for detection of a variety of toxins (Charych et al., *Chem. Biol.* 1996, 3, 113–20). We therefore fixed the $G_{M1}$ content at this level in all the doped systems throughout this study. When 5% $G_{M1}$ ganglioside was introduced into the L-Glu-Bis-3 system, a fair amount of vesicles were formed along with ribbons, as evidenced by the TEM micrographs (FIG. 4). The size of these vesicles varied from less than 100 nm to greater than 500 nm in diameter. A significant number of vesicles appeared to be attached to the ribbon structures, often at the junction of several entangled ribbons (FIG. 4B).

Incorporation of both $G_{M1}$ ganglioside and cholesterol as dopants. We introduced a third lipid component into the system. Incorporation of cholesterol, a structurally very different lipid, was studied up to a 20% molar concentration. At low cholesterol concentrations (5%), a uniform blue color was still attainable for the ternary assembly upon UV irradiation. However, with high cholesterol content (20%), only turbid suspensions could be obtained, even after prolonged vortexing or probe sonication, and polymerization became difficult. TEM micrographs of lipid systems doped with 5% and 10% cholesterol revealed that with increased cholesterol content, more vesicles were formed with continued coexistence of the ribbon structures (FIG. 4). Apparently, addition of cholesterol further facilitates and stabilizes the formation of vesicles. There were a significant amount of vesicles attached to ribbons (FIG. 4B) or nested on the framework of entangled ribbons (FIG. 4B). Budding and fission of vesicles were also observed (FIG. 4A).

Our results here clearly contradict any generalizations suggested in their study. In both systems studied here (the binary system doped with $G_{M1}$ and the ternary systems doped with both $G_{M1}$ and cholesterol), the dopants (such as glycosphingolipid and polycyclic cholesterol) are structurally very different from the bolaamphiphilic matrix lipid, and yet they were found to facilitate vesicle formation significantly. In the three-component systems, we speculate that cholesterol molecules are inserted in the outer-surface of the vesicles, filling the voids at the hydrophobic region between aggregated gangliosides and membrane spanning lipids. Given the fact that neither $G_{M1}$ ganglioside, cholesterol, nor membrane spanning matrix lipid L-Glu-Bis-3 by themselves assemble to form vesicles, it is apparent that inserting the proper dopants between membrane spanning lipids is essential to inducing surface curvature and vesicle formation.

An interesting morphological detail of the vesicle formation observed here was the presence of apparent budding and fission of vesicles (FIG. 4B). The multiple lipid components used here, and their inhomogeneous distribution within the systems observed, lead to the formation of phases with varied local lipid composition and surface curvature. When the surface curvature differences between various regions exceed a threshold, vesicle budding occurred. The budding process generates an energetically unfavorable line tension between neighboring domains that tends to diminish, leading to the eventual detachment of vesicles from their parental clusters.

Doping effect of a structurally compatible bolaamphiphile alone and in combination. Achiral and symmetric bolaamphiphile Bis-1 shares a structurally identical lipophilic core with L-Glu-Bis-3. When Bis-1 was introduced as a dopant, a different trend in morphological change was observed. With the incorporation of small amounts of Bis-1 (5% and 10%) in combination with 5% $G_{M1}$ ganglioside into the L-Glu-Bis-3 assembly, the microstructure remained predominantly a mixture of ribbons and vesicles, but with the emergence of a small amount of fragmented sheets (FIG. 5A). When the Bis-1 content was increased to 40%, the extended helical ribbons and vesicles disappeared completely, and were replaced with patches of flat, rectangular sheets (FIG. 5B).

The morphological outcome of doping Bis-1 is directly associated with the structural features of Bis-1 as compared to matrix lipid L-Glu-Bis-3. The structural similarity in the lipophilic core segment of the two lipids underlines the high miscibility of the lipids and establishes the role of Bis-1 as a structural 'diluting' agent. However, the difference in size, charge and chirality of the headgroups gives rise to the difference in the geometry of the lipid, the ability of forming H-bonding network at the surface, the chirality of the assembly at the supramolecular level, and eventually the morphological outcome of the mixed system. We believe that doping a high percentage (40%) of miscible lipid Bis-1 leads to interruption of the tight, crystalline chiral packing induced by the wedge-shaped bolaamphiphile (L-Glu-Bis-3) and ultimately prohibits the formation of extended helical ribbons. It is known that both general thermodynamic constraints and the geometry of each amphiphilic molecule present in a lipid matrix are crucial factors in determining the final shape and morphology of the aggregates formed (Israelachvili et al., *J Chem. Soc.—Faraday Trans. II* 1976, 72, 1525–1568). The dramatic morphological change observed here in the membrane spanning system doped with a high content of Bis-1 supports the important role of geometry and continued chiral packing of the constituent lipids in the formation of extended helical ribbon structures.

Morphological transformation between vesicles and ribbons. FIG. 5 highlights the morphological details of some distinctive microstructures observed for the doped L-Glu-Bis-3 assemblies. It is clear from these micrographs that ribbons (relatively rigid) and vesicles (relatively fluid) were physically interrelated during the formation of different assemblies.

Heterogeneity in lipid composition and distribution was first reflected by domain separations that were observed with large size vesicular structures. For large vesicles formed with multi-component lipids, especially for mixtures of polymerizable and unpolymerizable lipids, domain separation is expected (Gaub et al., *Biophys. J.* 1984, 45, 725–731). This is most clearly shown in FIG. 4B, where circular domains up to 100 nm in diameter are scattered throughout a large vesicle. Formation of these domains suggests the fluid nature of vesicular microstructures, where lateral diffusion and reorganization readily occurs. Indeed, domain separation was predominantly observed with large vesicles rather than with extended helical ribbon structures, arguably as a result of the higher concentrations of unpolymerizable $G_{M1}$ and cholesterol, and therefore higher fluidity within these vesicles.

A vesicle-to-ribbon transition mechanism at the periphery of some of the vesicles was suggested based on the observed morphological details of interconnected microstructures shown in FIGS. 4A (doped with 5% $G_{M1}$) and 4B (doped with 5% $G_{M1}$ and 5% cholesterol). The edges of vesicles or vesicle domains were outlined in the shape of ribbons. Such morphological details were observed for all mixed systems studied. The growth of a ribbon and its extension away from a vesicular microstructure is most clearly seen in the image shown in FIG. 4B. A vesicle-to-ribbon transition is a probable process during domain reorganizations within less crosslinked and more fluid microstructures. Lateral reorganization of lipids within these areas may have resulted in phases or domains with particularly low dopant concentrations, thus having a higher continuity of chirally packed matrix lipid L-Glu-Bis-3. Apparently it is at the edge of such domains that the transformation into more rigidly packed helical ribbons occurs.

It is worth noting that these inter-connected vesicle-ribbon structures are stable over time. We observed similar morphologies of samples stored at 4° C. for over a week. Further kinetic studies involving trapping at various intermediate stages of the microstructure transformation between vesicles and ribbons will be helpful for understanding of the process on a much shorter time scale.

EXAMPLE 7

Detection of Colorimetric and Morphological Transformation of Bolaamphiphilic Lipids UV-Visible and FTIR Spectroscopy. Visible absorption spectra were recorded on a Shimadzu UV-1601 spectrometer at ambient temperature. Poly-L-Glu-Bis-3 (0.3mg/ml, 0.1 N aq. NaCl) was diluted 10 fold (with 0.1 N aq. NaCl) before the absorption spectrum was taken. The sample was then passed through a 1 μm membrane (Whatman 4 mm syringe filter, polysulfone filter with polypropylene housing). The colorless filtrate was collected and its absorption spectrum recorded as above. FTIR spectra were obtained on a Perkin-Elmer System 2000 FTIR spectrometer. Solid sample was well ground with dry KBr powder and compressed into a transparent disk.

Dynamic Light Scattering (DSL) Experiments. Size distributions of the supramolecular aggregates were determined using a Coulter N4 Plus particle analyzer with a 90-degree detector angle. A 200 nm latex bead standard was used for calibration.

Transmission Electron Microscopy (TEM). TEM images of the supramolecular aggregates were obtained on both polymerized and un-polymerized forms using a Zeiss electron microscope operating at 80 kV. Samples were freshly made and deposited on carbon film coated Cu grids. Though the microstructures of diacetylene lipids are readily visualizable owing to the high electron density, negative staining with 0.5% uranyl acetate was performed to enhance the image quality.

Measurements of Colorimetric Response (CR) as a function of pH. Freshly cross-linked Poly-L-Glu-Bis-3 solution was loaded on a 96-well transparent tissue culture plate (100 μl per well). 2 μl of a sodium hydroxide solution (with a gradient of $[OH^-]$ from 6 M to $10^{-4}$ M) was added to each, well. The resulting solutions were then allowed to stand at ambient temperature for 30 min to stabilize the blue-to-red color change. The pHs of the resulting solutions were measured by a Coming Semi-micro pH Electrode (epoxy body). The calorimetric response (CR) to the pH increase was then recorded on a SPECTRAmax™ 250 Microplate Spectrophotometer supported by a SOFTmax PRO Microplate Analysis software (Molecular Devices Corporation). CR was measured as the percent change in the absorption at 630 nm (blue form polydiacetylene) relative to the total absorption at 630 nm and 550 nm (red form polydiacetylene). The initial percentage of blue phase is defined as $B_0=I_{630}/(I_{630}+I_{550})$. The same value was calculated for the pH elevated solution ($B_{pH}$). CR is therefore defined as the percentage change in blue form (B) upon the addition of base: $CR=[(B_0-B_{pH})/B_0]\times 100\%$.

Atomic Force Microscopy (AFM). 10 μl of crosslinked L-Glu-Bis-3 (0.15 mg/ml, in 0.1 N aq. NaCl) was spin-coated on a freshly cleaved Muscovite mica substrate. AFM was obtained on a home built instrument controlled by a commercial electronics unit (RHK Technology, Troy, Mich.). The AFM was enclosed in a box with ambient conditions of 21° C. and approximately 50% relative humidity. One silicon cantilever (Park Scientific Instruments) with a nominal force constant of 0.4 N/m and a measured tip radius of 150 nm was used.

Circular Dichroism (CD) Spectroscopy. CD measurements were performed on both the crosslinked Poly-L-Glu-Bis-3 (0.15 mg/ml, in 0.1 N aq. NaCl) and the pH elevated polymer sample. For the latter, 10% volume of pH 9 Tris buffer (25 mM Tris, 0.1 N aq. NaCl) was added to the Poly-L-Glu-Bis-3 (0.15 mg/ml, in 0.1 N aq. NaCl). The original homogeneous blue solution turned red instantly upon the addition of the buffer. CD spectra were recorded on a JASCO J-600 spectropolarimeter.

EXAMPLE 8

Using Bolaamphiphilic Lipids to Make LB Films for Biosensor Application

To enhance the adhesion of LB films to the solid substrate, glass slides were made hydrophilic by derivitization with amino silane. Terminal amines were then protonated by exposing the slides to HCl vapor, producing a positively charged surface. The carboxyl headgroups of bolaamphiphilic-lipid-containing PDA films strongly interact with and thus stably adhere to the hydrophilic, positively charged glass coating. Bolaamphiphilic lipids doped with 5% $G_{M1}$ ganglioside receptor (200), cholesterol and sc-Cys-PDA can then be compressed into monolayers, and horizontal transfer established film assemblies as that sensing interface on derivatized slides. As illustrated in FIG. 9, double-sided monolayers and multiple layers can be conveniently obtained by adopting various transfer schemes. To bond multiple layers, poly(allylamine) hydrochloride was used as an adhesion reagent. In this case, a double-sided monolayer biosensor was used.

Figure 6:
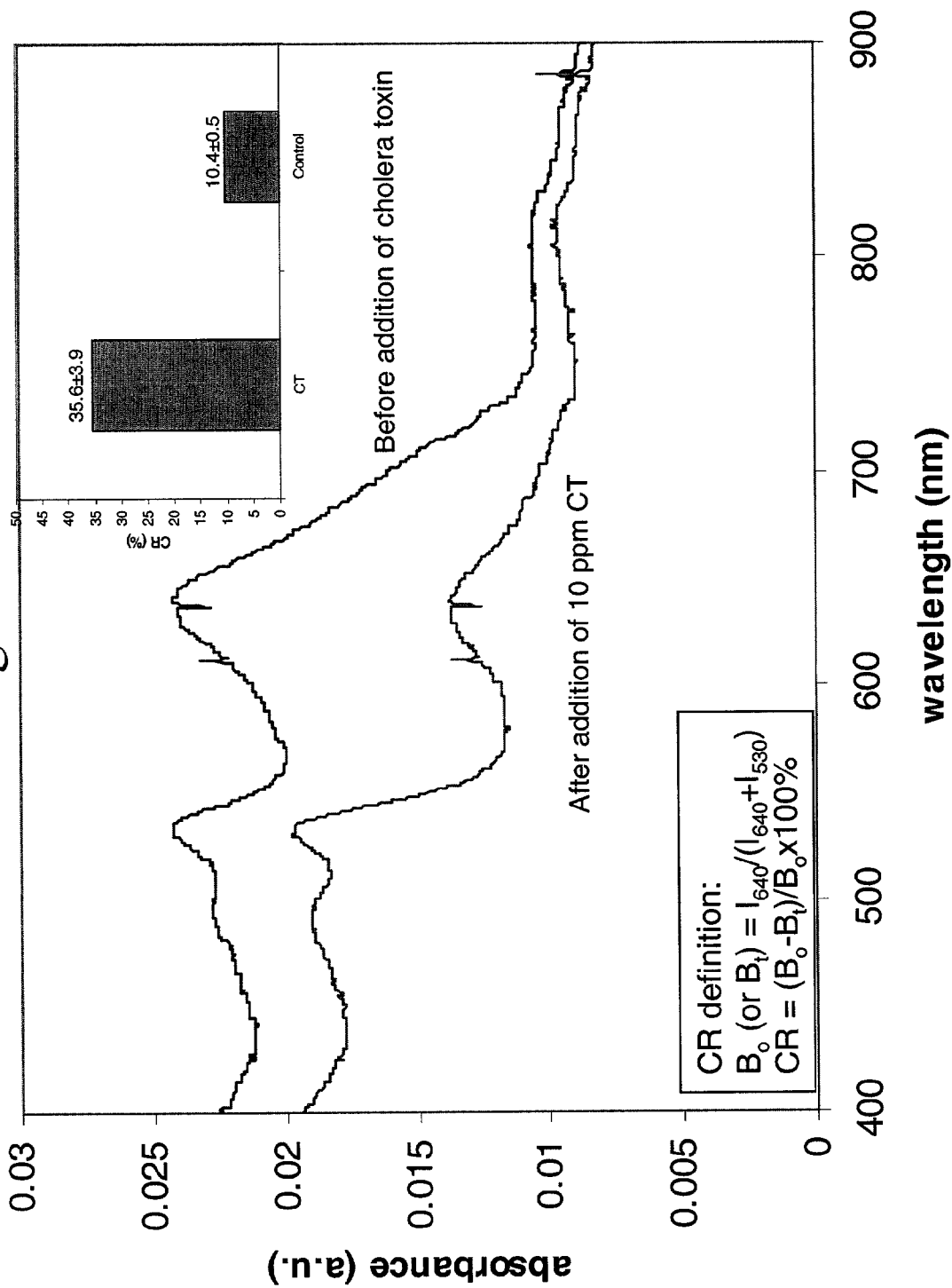
FIG. 6. UV spectra of a LB film sensor comprised of Bis-1 and $G_{M1}$ ganglioside doped with cholesterol and sc-Cys-PDA showing the absorption spectrum of the film before and after the addition of cholera toxin. The top curve is the absorption spectrum of the film before the addition of toxin and the bottom curve is the absorption spectrum immediately after addition of 10 ppm cholera toxin. The colorimetric response (CR) of the biosensor was calculated using the CR definition: $B_o$ (or $B_t$)=$I_{640}/(I_{640}+I_{530})$; CR=$(B_o-B_t)/B_o$×100%. The CR response after addition of cholera toxin and the control non-binding protein is shown in the bar graph in the top right-hand corner.
Figure 7:
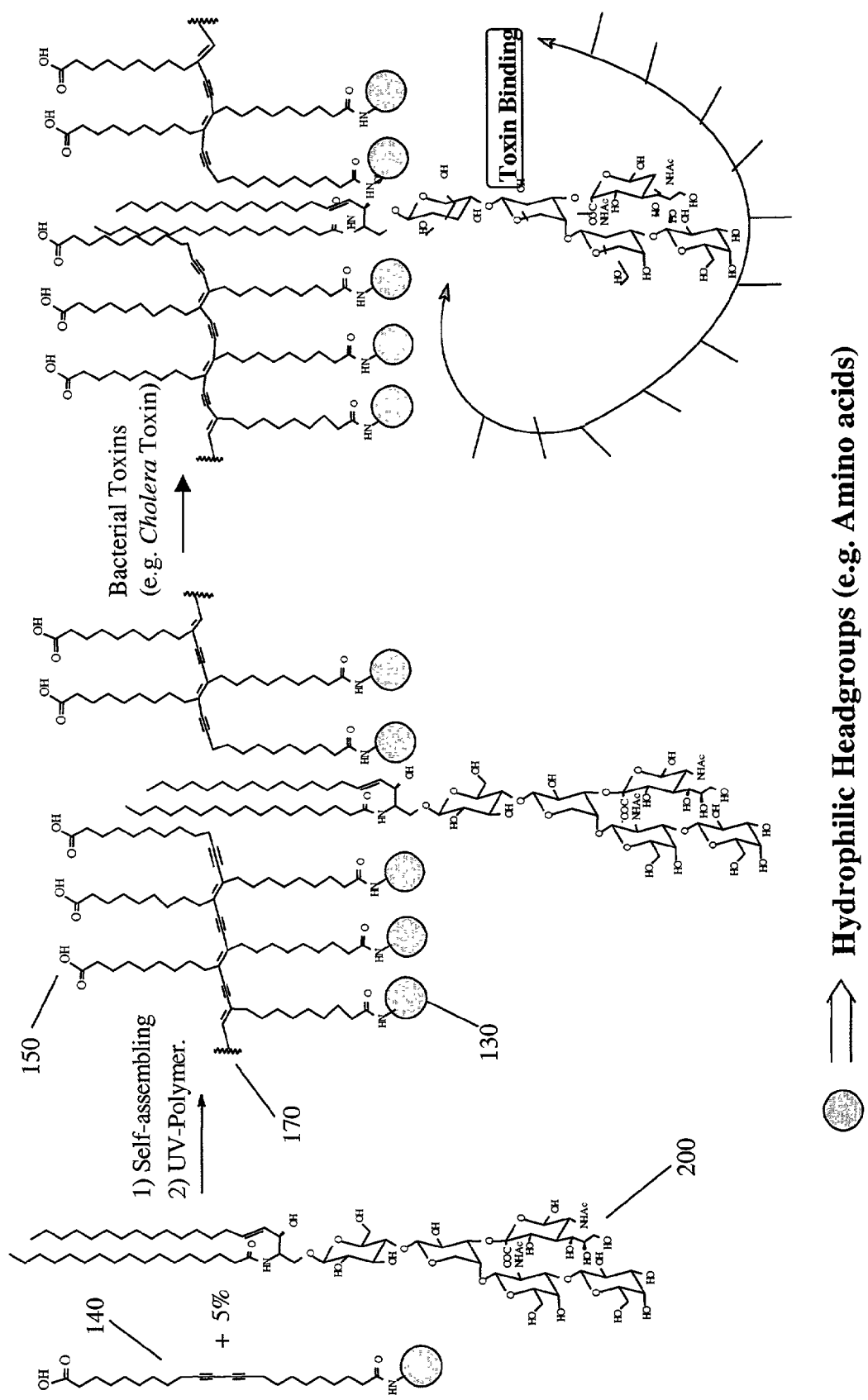
FIG. 7. Representation of a composition comprised of a bolaamphiphilic lipid doped with 5% $G_{M1}$ ganglioside (200) before and after the addition and binding of cholera toxin to the $G_{M1}$ receptor. Note the change in bond angles of the ene-yne bonds (in-plane vs. out-of-plane) which is thought to account for the change in composition color from blue to red upon toxin binding.

The double-sided monolayer biosensor, comprised of Bis-1 and 5% $G_{M1}$ ganglioside, doped with cholesterol and sc-Cys-PDA, was contacted with samples containing cholera toxin. FIG. 6 shows the UV spectra of the sensor showing the absorption spectrum of the film before and after the addition of cholera toxin (CT). The top curve is the absorption spectrum of the film before the addition of toxin and the bottom curve is the absorption spectrum immediately after addition of 10 ppm cholera toxin. The calorimetric response (CR) of the biosensor was calculated using the CR definition: $B_o$ (or $B_t$)=$I_{640}/(I_{640}+I_{530})$; CR=$(B_o-B_t)/B_o \times$ 100%. The CR response after addition of cholera toxin and the control non-binding protein is shown in the bar graph in the top right-hand corner.

Also in data not shown, at 10 ppm CT level, the calorimetric response is almost 36%, compared with a colorimetric response of less than 8% at the same CT concentration with a bilayer PDA film sensor. Thus, the increased rigidity of bolaamphiphilic lipids provides a higher sensitivity and colorimetric response than traditional bilayer film sensors.

EXAMPLE 9

Using Bolaamphiphilic Lipids for Tissue Engineering

One area that bolaamphiphilic polydiactylene nanoribbons/tubes can play an important role in is tissue engineering, such as bone replacement or the fabrication of artificial bone-like materials. Natural bone is a composite of collagen, a protein template periodically decorated with acidic phosphoproteins, and the inorganic material hydroxyapatite. Many essential biological activities of bone, from its metabolism, repair to the dynamic building or resorption, are all known to be associated with and influenced by changes of bone structure on a nanoscopic level. For instance, bone nanocrystal (apatites) growth is driven by phosphoprotein templating at the molecular level. To achieve highly controlled mineralization in the design of artificial bonelike material, a highly ordered molecular template is required. Previous efforts of using self-assembling materials for directing mineral growth have been limited to amphiphilic lipid based surface modification. The highly ordered arrangement of surface anionic groups of the bolamamphiphilic lipids (hexagonal or distorted hexagonal/pseudo-rectangular packing arrangement) can provide a bulk scaffold for making artificial bones.

What is claimed is:

1. A composition comprising a plurality of polymerized self-assembled bolaamphiphilic bisfunctional diacetylene lipids, each lipid comprising a hydrophobic hydrocarbon core, an anionic head group and an oxy acid end group, wherein said anionic head group comprises an amino acid, and whereby exposure to a pH of 5.8 or greater induces a color-coded biphasic transformation of said composition.

2. The composition of claim 1, wherein the color-coded biphasic transformation comprises a transition from blue helical ribbons and wide sheets to organized red nanofibers.

3. The composition of claim 1, wherein said polymerized self-assembled bolaamphiphilic bisfunctional diacetylene lipids are self assembled into right-handed helical ribbons and wide sheets with micron scale length and nano scale thickness.

4. The composition of claim 1, whereby exposure to pH from about 5.8 to about 9.8 induces a color-coded biphasic transformation of said composition.

5. The composition of claim 4, wherein the pH is between about 7.2 and 9.0.

6. The composition of claim 5, wherein the pH is between about 7.2 and 7.5.

7. The composition of claim 1, wherein the anionic headgroup is selected from the group consisting of: glutamic acid, aspartic acid, glutamate, aspartate, serine, phosphoserine, threonine, glutamine, asparagine, DL-Homocystic acid, and peptide combinations or any natural or unnatural analogs thereof.

8. The composition of claim 1, wherein the oxy acid end group is selected from the group consisting of: carboxylic acid, hydroxyl groups, amino acids, amino acid derivatives, and combinations thereof.

9. An optically active polymer comprising a plurality of polymerized self-assembled asymmetric bolaamphiphilic bisfunctional diacetylene lipids, wherein each lipid has a hydrophobic hydrocarbon core, an L-glutamic acid headgroup and an oxy acid end group, whereby exposure to a pH of 5.8 or greater induces a color-coded biphasic transformation of said polymer.

10. The polymer of claim 9, wherein the color-coded transition and morphological transformation comprises a transition from blue helical ribbons and wide sheets to organized red nanofibers.

11. The polymer of claim 10, wherein the polymer is self-assembled into right-handed helical ribbons and wide sheets.

12. The polymer of claim 11, whereby upon exposure of the polymer to pH from about 5.8 to about 9.8 induces a color-coded biphasic transformation of said polymer.

13. The polymer of claim 12, wherein the pH is between about 7.2 and 9.0.

14. The polymer of claim 13, wherein the pH is between about 7.2 and 7.5.

15. A method for pH induced morphological transformation and chromatic transition in an optically active polymer,
 a. providing a polymer comprising a plurality of polymerized self-assembled bolaamphiphilic bisfunctional diacetylene lipids, each lipid having a hydrophobic hydrocarbon core, an L-glutamic acid head group and a carboxyl group end group; and
 b. subjecting said polymer to a treatment with increasing pH levels, said levels from about 5.8 to 9.8.

* * * * *